United States Patent
Zhang et al.

(10) Patent No.: US 11,858,976 B2
(45) Date of Patent: Jan. 2, 2024

(54) NUCLEIC ACID CONSTRUCTS ENCODING CHIMERIC NK RECEPTOR, CELLS CONTAINING, AND THERAPEUTIC USE THEREOF

(71) Applicant: THE TRUSTEES OF DARTMOUTH COLLEGE, Hanover, NH (US)

(72) Inventors: Tong Zhang, Beijing (CN); Charles L Sentman, West Lebanon, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 17/841,117

(22) Filed: Jun. 15, 2022

(65) Prior Publication Data

US 2022/0402996 A1 Dec. 22, 2022

Related U.S. Application Data

(60) Division of application No. 17/748,683, filed on May 19, 2022, which is a division of application No. 16/458,740, filed on Jul. 1, 2019, now Pat. No. 11,339,199, which is a division of application No. 14/600,799, filed on Jan. 20, 2015, now Pat. No. 10,336,804, which is a continuation of application No. 12/407,440, filed on Mar. 19, 2009, now abandoned, which is a continuation-in-part of application No. 11/575,878, filed as application No. PCT/US2005/031100 on Aug. 31, 2005, now Pat. No. 7,994,298.

(60) Provisional application No. 60/681,782, filed on May 17, 2005, provisional application No. 60/612,836, filed on Sep. 24, 2004.

(51) Int. Cl.
| C07K 14/705 | (2006.01) |
| A61K 38/10 | (2006.01) |
| C07K 14/715 | (2006.01) |
| A61K 35/17 | (2015.01) |
| A61K 45/06 | (2006.01) |

(52) U.S. Cl.
CPC ............ *C07K 14/705* (2013.01); *A61K 35/17* (2013.01); *A61K 38/10* (2013.01); *A61K 45/06* (2013.01); *C07K 14/715* (2013.01)

(58) Field of Classification Search
CPC .................................................. C07K 14/705
See application file for complete search history.

(56) References Cited

U.S. PATENT DOCUMENTS

| 5,359,046 A | 10/1994 | Capon et al. |
| 5,415,874 A | 5/1995 | Bender et al. |
| 5,552,300 A | 9/1996 | Makrides et al. |
| 5,667,967 A | 9/1997 | Steinman et al. |
| 5,686,281 A | 11/1997 | Roberts |
| 5,830,755 A | 11/1998 | Nishimura et al. |
| 5,851,828 A | 12/1998 | Seed et al. |
| 6,103,521 A | 8/2000 | Capon et al. |
| 6,284,240 B1 | 9/2001 | Seed et al. |
| 6,407,221 B1 | 6/2002 | Capon et al. |
| 6,407,319 B1 | 6/2002 | Rose-Fricker et al. |
| 6,410,319 B1 | 6/2002 | Raubitschek et al. |
| 6,464,978 B1 | 10/2002 | Brostoff et al. |
| 6,753,162 B1 | 6/2004 | Seed et al. |
| 6,770,749 B2 | 8/2004 | Ellenhorn et al. |
| 6,984,382 B1 | 1/2006 | Groner et al. |
| 7,049,136 B2 | 5/2006 | Seed et al. |
| 7,052,906 B1 | 5/2006 | Lawson et al. |
| 7,070,995 B2 | 7/2006 | Jensen |
| 7,094,599 B2 | 8/2006 | Seed et al. |
| 7,446,179 B2 | 11/2008 | Jensen et al. |
| 7,446,190 B2 | 11/2008 | Sadelain et al. |
| 7,456,263 B2 | 11/2008 | Sherman et al. |
| 7,514,537 B2 | 4/2009 | Jensen |
| 7,569,357 B2 | 8/2009 | Kranz et al. |
| 7,608,410 B2 | 10/2009 | Dunn et al. |
| 7,618,817 B2 | 11/2009 | Campbell |
| 7,655,461 B2 | 2/2010 | Finn et al. |
| 7,763,243 B2 | 7/2010 | Lum et al. |
| 7,820,174 B2 | 10/2010 | Wang et al. |
| 7,994,298 B2 | 8/2011 | Zhang et al. |
| 8,252,914 B2 | 8/2012 | Zhang et al. |
| 8,283,446 B2 | 10/2012 | Jakobsen et al. |
| 8,465,743 B2 | 6/2013 | Rosenberg et al. |
| 8,519,100 B2 | 8/2013 | Jakobsen et al. |

(Continued)

FOREIGN PATENT DOCUMENTS

| DE | 4408999 | 9/1995 |
| DE | 19540515 | 6/1997 |

(Continued)

OTHER PUBLICATIONS

Yu, T K et al. "IL-2 activation of NK cells: involvement of MKK1/2/ERK but not p38 kinase pathway." Journal of Immunology (Baltimore, Md. : 1950) vol. 164,12 (2000): 6244-51. doi:10.4049/jimmunol.164.12.6244.

(Continued)

*Primary Examiner* — Anoop K Singh
*Assistant Examiner* — David A Montanari
(74) *Attorney, Agent, or Firm* — Robin L. Teskin; Baker, Donelson, Bearman, Caldwell & Berkowitz PC

(57) ABSTRACT

The present invention relates to chimeric immune receptor molecules for reducing or eliminating tumors. The chimeric receptors are composed a C-type lectin-like natural killer cell receptor, or a protein associated therewith, fused to an immune signaling receptor containing an immunoreceptor tyrosine-based activation motif. Methods for using the chimeric receptors are further provided.

22 Claims, 7 Drawing Sheets

Specification includes a Sequence Listing.

(56) References Cited

U.S. PATENT DOCUMENTS

| | | |
|---|---|---|
| 8,956,828 B2 | 2/2015 | Bonini et al. |
| 2001/0007152 A1 | 7/2001 | Sherman et al. |
| 2002/0045241 A1 | 4/2002 | Schendel |
| 2002/0102691 A1 | 8/2002 | Davis et al. |
| 2002/0137697 A1 | 9/2002 | Eshhar et al. |
| 2003/0060444 A1 | 3/2003 | Finney et al. |
| 2003/0077249 A1 | 4/2003 | Bebbington et al. |
| 2003/0082719 A1 | 5/2003 | Schumacher et al. |
| 2003/0093818 A1 | 5/2003 | Belmont et al. |
| 2003/0219463 A1 | 11/2003 | Falkenburg et al. |
| 2004/0038886 A1 | 2/2004 | Finney et al. |
| 2004/0115198 A1 | 6/2004 | Spies et al. |
| 2004/0259196 A1 | 12/2004 | Zipori et al. |
| 2005/0048055 A1 | 3/2005 | Newell et al. |
| 2005/0129671 A1 | 6/2005 | Cooper et al. |
| 2005/0238626 A1 | 10/2005 | Yang et al. |
| 2006/0247420 A1 | 2/2006 | Coukos et al. |
| 2006/0093605 A1 | 5/2006 | Campana et al. |
| 2006/0166314 A1 | 7/2006 | Voss et al. |
| 2006/0263334 A1 | 11/2006 | Finn et al. |
| 2006/0269529 A1 | 11/2006 | Niederman et al. |
| 2007/0066802 A1 | 3/2007 | Geiger |
| 2007/0077241 A1 | 4/2007 | Spies et al. |
| 2007/0116690 A1 | 5/2007 | Yang et al. |
| 2008/0199424 A1 | 8/2008 | Yang et al. |
| 2008/0292549 A1 | 11/2008 | Jakobsen et al. |
| 2008/0292602 A1 | 11/2008 | Jakobsen et al. |
| 2009/0053184 A1 | 2/2009 | Morgan et al. |
| 2009/0202501 A1 | 8/2009 | Zhang et al. |
| 2009/0226404 A1 | 9/2009 | Schuler et al. |
| 2009/0304657 A1 | 12/2009 | Morgan et al. |
| 2009/0324566 A1 | 12/2009 | Shiku et al. |
| 2010/0009863 A1 | 1/2010 | Himmler et al. |
| 2010/0015113 A1 | 1/2010 | Restifo et al. |
| 2010/0029749 A1 | 2/2010 | Zhang et al. |
| 2010/0055117 A1 | 3/2010 | Krackhardt et al. |
| 2010/0104556 A1 | 4/2010 | Blankenstein et al. |
| 2010/0105136 A1 | 4/2010 | Carter et al. |
| 2010/0135974 A1 | 6/2010 | Eshhar et al. |
| 2010/0143315 A1 | 6/2010 | Voss et al. |
| 2010/0178276 A1 | 7/2010 | Sadelain et al. |
| 2010/0189728 A1 | 7/2010 | Schendel et al. |
| 2011/0158957 A1 | 6/2011 | Bonini et al. |
| 2012/0252742 A1 | 10/2012 | Kranz et al. |
| 2012/0294857 A1 | 11/2012 | Sentman et al. |
| 2012/0302466 A1 | 11/2012 | Sentman et al. |
| 2013/0011375 A1 | 1/2013 | Chen |
| 2013/0323214 A1 | 12/2013 | Gottschalk et al. |
| 2014/0004132 A1 | 1/2014 | Brenner et al. |
| 2019/0338011 A1 | 11/2019 | Zhang et al. |

FOREIGN PATENT DOCUMENTS

| | | |
|---|---|---|
| DE | 10259713 | 8/2004 |
| EP | 0340793 | 8/1995 |
| EP | 0499555 | 5/2000 |
| EP | 0574512 | 5/2003 |
| EP | 1226244 | 7/2004 |
| EP | 0871495 | 6/2005 |
| EP | 1075517 | 7/2006 |
| EP | 1932537 | 6/2008 |
| EP | 1765860 | 10/2008 |
| EP | 2186825 | 5/2010 |
| EP | 1791865 | 7/2010 |
| JP | 05176760 | 7/1993 |
| WO | WO 1991018019 | 11/1991 |
| WO | WO 1992015322 | 9/1992 |
| WO | WO 1994024282 | 10/1994 |
| WO | WO 1996015238 | 5/1996 |
| WO | WO 1996013584 | 9/1996 |
| WO | WO 1998018809 | 7/1998 |
| WO | WO 1998041613 | 9/1998 |
| WO | WO 2000031239 | 2/2000 |
| WO | WO 2000014257 | 3/2000 |
| WO | WO 2001092291 | 6/2001 |
| WO | 200191625 | 12/2001 |
| WO | WO 02/068615 | 9/2002 |
| WO | WO 2004056845 | 8/2004 |
| WO | WO 2006103429 | 5/2006 |
| WO | WO 2006060878 | 6/2006 |
| WO | WO 2009059804 | 5/2009 |
| WO | WO 2009091826 | 7/2009 |
| WO | WO 2010012829 | 4/2010 |
| WO | WO 2010025177 | 4/2010 |
| WO | WO 2010058023 | 5/2010 |
| WO | WO 2010088160 | 5/2010 |
| WO | WO 2010037395 | 8/2010 |
| WO | WO 2010107400 | 9/2010 |
| WO | WO 2011059836 | 5/2011 |
| WO | WO 2012050374 | 4/2012 |
| WO | WO 2013166051 | 11/2013 |

OTHER PUBLICATIONS

Moretta, A et al. "Activating receptors and coreceptors involved in human natural killer cell-mediated cytolysis." Annual review of immunology vol. 19 (2001): 197-223. doi:10.1146/annurev.immunol. 19.1.197.

Bruhns, P et al. "Differential roles of N- and C-terminal immunoreceptor tyrosine-based inhibition motifs during inhibition of cell activation by killer cell inhibitory receptors." Journal of immunology (Baltimore, Md. : 1950) vol. 162,6 (1999): 3168-75.

Abken H, et al. "Immune response manipulation: recombinant immunoreceptors endow T-cells with predefined specificity," Curr Pharm Des. 2003;9(24):1992-2001.

Beecham EJ, et al. "Coupling CD28 co-stimulation to immunoglobulin T-cell receptor molecules: the dynamics of T-cell proliferation and death," J Immunother. Nov.-Dec. 2000-23(6):631-42.

Beecham EJ, et al. 'Dynamics of tumor cell killing by human T lymphocytes armed with an anti-carcinoembryonic antigen chimeric immunoglobulin T-cell receptor.' J Immunother. May-Jun. 2000;23(3):332-43.

Billadeau DD, et al. 'NKG2D-DAP10 triggers human NK cell-mediated killing via a Syk-independent regulatory pathway.' Nat Immunol. Jun. 2003;4(6):557-64. Epub May 11, 2003.

Brocker T, et al. "Adoptive tumor immunity mediated by lymphocytes bearing modified antigen-specific receptors," Adv Immunol. 1998;68:257-69.

Calogero A, et al. "Recombinant T-cell receptors: an immunologic link to cancer therapy," J Immunother. Jul.-Aug. 2000;23(4):393-400.

Cooper LJ, et al. "Enhanced antilymphoma efficacy of CD19-redirected influenza MP1-specific CTLs by cotransfer of T cells modified to present influenza MP1," Blood. Feb. 15, 2005;105(4):1622-31.

Costa GL, et al. "Targeting rare populations of murine antigen-specific T lymphocytes by retroviral transduction for potential application in gene therapy for autoimmune disease," J Immunol. Apr. 1, 2000;164(7):3581-90.

Dall P, et al. 'In vivo cervical cancer growth inhibition by genetically engineered cytotoxic T cell' Cancer Immunol Immunother. Jan. 2005;54(1):51-60.

Daly T, et al. "Recognition of human colon cancer by T cells transduced with a chimeric receptor gene," Cancer Gene Ther. Feb. 2000;7(2):284-91.

Darcy PK, et al. "Redirected perforin-dependent lysis of colon carcinoma by ex vivo genetically engineered CTL," J Immunol. Apr. 1, 2000;164(7):3705-12.

Eshhar Z, et al. 'Specific activation and targeting of cytotoxic lymphocytes through chimeric single chains consisting of antibody-binding domains and the gamma or zeta subunits of the immunoglobulin and T-cell receptors.' Proc Natl Acad Sci U S A. Jan. 15, 1993;90(2):720-4.

Finney HM, et al. "Activation of resting human primary T cells with chimeric receptors: costimulation from CD28, inducible costimulator, CD134, and CD137 in series with signals from the TCR zeta chain," J Immunol. Jan. 1, 2004;172(1):104-13.

(56) References Cited

OTHER PUBLICATIONS

Finney HM, et al. 'Chimeric receptors providing both primary and costimulatory signaling in T cells from a single gene product.' J Immunol. Sep. 15, 1998;161(6):2791-7.
Fitzer-Attas CJ, et al. "Tyrosine kinase chimeras for antigen-selective T-body therapy," Adv Drug Deliv Rev. Apr. 6, 1998;31(1-2):171-182.
Garrity D, et al. 'The activating NKG2D receptor assembles in the membrane with two signaling dimers into a hexameric structure.' Proc Natl Acad Sci U S A. May 24, 2005;102(21):7641-6. Epub May 13, 2005.
Gilham DE, et al. "Primary polyclonal human T lymphocytes targeted to carcino-embryonic antigens and neural cell adhesion molecule tumor antigens by CD3zeta-based chimeric immune receptors," J Immunother. Mar.-Apr. 2002;25(2):139-51.
Groh V, et al. "Costimulation of CD8alphabeta T cells by NKG2D via engagement by MIC induced on virus-infected cells," Nat Immunol. Mar. 2001;2(3):255-60.
Guest RD, et al. "The role of extracellular spacer regions in the optimal design of chimeric immune receptors: evaluation of four different scFvs and antigens," J Immunother. May-Jun. 2005;28(3):203-11.
Haynes NM, et al. 'Redirecting Mouse CTL Against Colon Carcinoma: Superior Signaling Efficacy of Single-Chain Variable Domain Chimeras Containing TCR-ζvs FcεRI-γ' J Immunol. Jan. 1, 2001;166(1):182-7.
Hege KM, et al. "T-cell gene therapy," Curr Opin Biotechnol. Dec. 1996;7(6):629-34.
Ho WY, et al. "Adoptive immunotherapy: engineering T cell responses as biologic weapons for tumor mass destruction," Cancer Cell. May 2003;3(5):431-7.
Hombach A, et al. "Grafting T cells with tumor specificity: the chimeric receptor strategy for use in immunotherapy of malignant diseases," Hybridoma. Feb. 1999;18(1):57-61.
Imai C, et al. "Chimeric receptors with 4-1BB signaling capacity provoke potent cytotoxicity against acute lymphoblastic leukemia," Leukemia. Apr. 2004; 18(4):676-84.
Imai C, et al. "T-Cell immunotherapy for B-lineage acute lymphoblastic leukemia using chimeric antigen receptors that deliver 4-1BB-mediated costimulatory signals," Blood. Nov. 16, 2003;102(11):66A-67A.
Imai et al. "Genetic modification of T cells for cancer therapy," J Biol Regul Homeost Agents. Jan.-Mar. 2004;18(1):62-71.
Junghans RP. "Designer T Cells for Breast Cancer Therapy: Phase I Studies," Beth Israel Deaconess Medical Center, Boston, Massachusetts; 2001. 85 pages.
Lamers CH, et al. "Protocol for gene transduction and expansion of human T lymphocytes for clinical immunogene therapy of cancer," Cancer Gene Ther. Jul. 2002;9(7):613-23.
Lampson LA. "Beyond inflammation: site-directed immunotherapy," Immunol Today. Jan. 1998;19(1):17-22.
Liao KW, et al. "Design of transgenes for efficient expression of active chimeric proteins on mammalian cells," Biotechnol Bioeng. May 20, 2001;73(4):313-23.
Losch FO, et al. 'Activation of T cells via tumor antigen specific chimeric receptors: the role of the intracellular signaling domain.' Int J Cancer. Jan. 20, 2003;103(3):399-407.
Ma Q, et al. "Anti-prostate specific membrane antigen designer T cells for prostate cancer therapy," Prostate. Sep. 15, 2004;61(1):12-25.
Ma Q, et al. "Genetically engineered T cells as adoptive immunotherapy of cancer," Cancer Chemother Biol Response Modif. 2002;20:315-41.
Maher J, et al. 'Human T-lymphocyte cytotoxicity and proliferation directed by a single chimeric TCRzeta /CD28 receptor.' Nat Biotechnol. Jan. 2002;20(1):70-5.
Meresse B, et al. 'Coordinated induction by IL15 of a TCR-independent NKG2D signaling pathway converts CTL into lymphokine-activated killer cells in celiac disease.' Immunity. Sep. 2004;21(3):357-66.

Moeller M, et al. 'A functional role for CD28 costimulation in tumor recognition by single-chain receptor-modified T cells.' Cancer Gene Ther. May 2004;11(5):371-9.
Motmans K, et al. 'Enhancing the tumor-specifity of human T cells by the expression of chimericimmunoglobulin/T cell receptor genes.' Immunotechnology, Nov. 1996;2(4): 303-304(2).
Muniappan A, et al. "Ligand-mediated cytolysis of tumor cells: use of heregulin-zeta chimeras to redirect cytotoxic T lymphocytes," Cancer Gene Ther. Jan. 2000;7(1):128-34.
Nguyen P, et al. 'Antigen-specific targeting of CD8+ T cells with receptor-modified T lymphocytes.' Gene Ther. Apr. 2003;10(7):594-604.
Nguyen P, et al. 'Identification of a murine CD28 dileucine motif that suppresses single-chain chimeric T-cell receptor expression and function.' Blood. Dec. 15, 2003;102(13):4320-5. Epub Aug. 28, 2003.
Pardoll DM. "Tumor reactive T cells get a boost," Nat Biotechnol. Dec. 2002;20(12):1207-8.
Patel SD et al. "T-cell killing of heterogenous tumor or viral targets with bispecific chimeric immune receptors," Cancer Gene Ther. Aug. 2000;7(8):1127-34.
Patel SD, et al. "Impact of chimeric immune receptor extracellular protein domains on T cell function," Gene Ther. Mar. 1999;6(3):412-9.
Pinthus JH, Eshhar Z. The T-body approach: towards cancer immunogene therapy. In: Stuhler G, Walden P, editors. Cancer Immune Therapy: Current and Future Strategies. John Wiley & Sons; 2002. p. 287-98.
Pule M, et al. "Artificial T-cell receptors," Cytotherapy. 2003;5(3):211-26.
Regueiro JR, Martín-Fernández JM, Melero I. Immunity and gene therapy: benefits and risks. Inmunología. 2004;23(1):56-62.
Rössig C, et al. "Chimeric T-cell receptors for the targeting of cancer cells," Acta Haematol. 2003;110(2-3):154-9.
Rossig C, et al. "Genetic modification of T lymphocytes for adoptive immunotherapy," Mol Ther. Jul. 2004;10(1):5-18.
Rossig Cl, et al. "Epstein-Barr virus-specific human T lymphocytes expressing antitumor chimeric T-cell receptors: potential for improved immunotherapy," Blood. Mar. 15, 2002;99(6):2009-16.
Schumacher TN. "T-cell-receptor gene therapy," Nat Rev Immunol. Jul. 2002;2(7):512-9.
Uherek C, et al. "Chimeric antigen receptors for the retargeting of cytotoxic effector cells," J Hematother Stem Cell Res. Aug. 2001;10(4):523-34.
Verneris MR, et al. 'Role of NKG2D signaling in the cytotoxicity of activated and expanded CD8+ T cells.' Blood. Apr. 15, 2004;103(8):3065-72. Epub Nov. 20, 2003.
Weijtens ME, et al. "A retroviral vector system 'STITCH' in combination with an optimized single chain antibody chimeric receptor gene structure allows efficient gene transduction and expression in human T lymphocytes," Gene Ther. Sep. 1998;5(9):1195-203.
Weijtens ME, et al. "Functional balance between T cell chimeric receptor density and tumor associated antigen density: CTL mediated cytolysis and lymphokine production," Gene Ther. Jan. 2000;7(1):35-42.
Weijtens MEM. "Immune-gene therapy for renal cancer chimeric receptor-mediated lysis of tumor cells," thesis, Erasmus University Rotterdam; 2001. 128 pages.
Willemsen RA, et al. "Genetic engineering of T cell specificity for immunotherapy of cancer," Hum Immunol. Jan. 2003;64(1):56-68.
Wu J, et al. 'An activating immunoreceptor complex formed by NKG2D and DAP10.' Science. Jul. 30, 1999;285(5428):730-2.
Report Listing Estimated New Cancer Cases and Deaths by Sex, United States American Cancer Society, Surveillance and Health Policy (2009).
Baba et al., "N-Linked Carbohydrate on Human Leukocyte Antigen-C and Recognition by natural Killer Cell Inhibitory Receptors", Human Immunology 20000 61:1202-1218.
Barber et al., "Chimeric NKG2D Receptor-Bearing T Cells as Immunotherapy for Ovarian Cancer," Cancer Research, vol. 67, No. 10 (2007).

(56) References Cited

OTHER PUBLICATIONS

Barber et al., "Chimeric NKG2D Receptor-Expressing T Cells as an Immunotherapy for Multiple Myeloma," Experimental Hematology, pp. 1-11 (2008).
Basu et al., "Estradiol Regulates MICA Expression in Human Endometrial Cells," Clinical Immunology, vol. 129, pp. 325-332 (2008).
Bauer et al., Activation of NK cells and T cells by NKG2D, a receptor for stress-inducible MICA, Science 285(5428): 727-729, 1999.
Belakova et al., DNA vaccines: are they still just a powerful tool for the future? Arch Immunol Ther Exp. (Warsz), 55(6): 387-398, 2007.
Boll et al., "Heat Shock protein 90 Inhibitor BIIB021 (CNF2024) Depletes NF-κB and Sensitizes Hodgkin Lymphoma Cells for Natural Killer Cell-Mediated Cytotoxicity," Clinical Cancer Research, vol. 15, No. 16 (2009).
Bonini et al., "HSV-TK Gene Transfer into Donor Lymphocytes for Control of Allogeneic Graft-Versus-Leukemia", Science 1997 276:1720-1724.
Cambier. "Antigen and Fc receptor signaling. The awesome power of the immunoreceptor tyrosine-based activation motif (ITAM)," J Immunol. Oct. 1, 1995;155(7):3281-5.
Chansac et al., "Potentiation of NK Cell-Mediated Cytotoxicity in Human Lung Adenocarcinoma: Role of NKG2D-Dependent Pathway," International Immunology, vol. 20, No. 7, pp. 801-810 (2008).
Chen et al., "NKG2D Ligands Expression and NKG2D-Mediated Cytotoxicity in Human Laryngeal Squamous Carcinoma Cells," Scandinavian Journal of Immunology, vol. 67, pp. 441-447 (2008).
Clay et al., "Efficient Transfer of a Tumor Antigen-Reactive TCR to Human Peripheral Blood Lymphocytes Confers Anti-Tumor Reactivity", The Journal of Immunology 1999 163:507-513.
Diefenbach et al., "Innate immune recognition by stimulatory immunoreceptors," Current Opinion in Immunology, 15(1): 37-44, 2003.
Diefenbach et al., The innate immune response to tumors and its role in the induction of T-cell immunity, Immunol Rev. 188: 9-21, 2002.
Duan et al., "Clinical Significance of the Immunostimulatory MHC Class I Chain-Related Molecule A and NKG2D Receptor on NK Cells in Pancreatic Cancer," Medical Oncology (2010).
Dulphy et al., "NKG2D Ligands Expression and NKG2D-Mediated NK Activity in Sezary Patients," Journal of Investigative Dermatology, vol. 129, pp. 359-364 (2009).
Eisele et al., "TGF-β and Metalloproteinases Differentially Suppress NKG2D Ligand Surface Expression on Malignant Glioma Cells," Brain, vol. 129, pp. 2416-2425 (2006).
Friese et al., "MICA/NKG2D-Mediated Immunogene Therapy of Experimental Gliomas," Cancer Research, vol. 63, pp. 8996-9006 (2003).
Gilham et al., "Primary polyclonal human T lymphocytes targeted to carcino-embryonic antigens and neural cell adhesion molecule tumor antigens by CD3zeta-based chimeric immune receptors," J. Immunother, Mar.-Apr. 2002: 25(2): 139-151, 2002.
Girlanda et al., "MICA Expressed by Multiple Myeloma and Monoclonal Gammopathy of Undetermined Significance Plasma Cells Costimulates Pamidronate-Activated γδ Lymphocytes," Cancer Research, vol. 65, No. 16, pp. 7502-7508 (2005).
Gonzalez et al., "Genetic engineering of cytolytic T lymphocytes for adoptive T-cell therapy of neuroblastoma", J Gene Med 2004 6:704-711.
Groh et al., "Broad Tumor-Associated Expression and Recognition by Tumor-Derived γδT Cells of MICA and MICB," Proceedings of the National Academy of Sciences, vol. 96, pp. 6879-6884 (1999).
Heuser et al., "T-cell activation by recombinant immunoreceptors: impact of the intracellular signalling domain on the stability of receptor expression and antigen-specific activation of grafted T-cells," Gene Therapy 10: 1408-1419, 2003.

Houchins et al., "DNA sequence analysis of NKG2, a family of related cDNA clones encoding type II integral membrane proteins on human natural killer clees," J Exp. Med. 173(4): 1017-1020, 1991.
Inagaki et al., "Expression of the ULBP Ligands for NKG2D by B-NHL Cells Plays an Important Role in Determining Their Susceptibility to Rituximab-Induced ADCC," International Journal of Cancer, vol. 125, pp. 212-221 (2009).
Jinushi et al., "Expression and Role of MICA and MICB in Human Hepatocellular Carcinomas and Their Regulation by Retinoic Acid," International Journal of Cancer, vol. 104, pp. 354-361 (2003).
Liu et al., "MICA and MICB Overexpression in Oral Squamous Cell Carcinoma," Journal of Oral Pathology and Medicine, vol. 36, pp. 43-47 (2007).
Lowin-Kropf et al., "Cytoskeletal polarization of T cells is regulated by an immunoreceptor tyrosine-based activation motif-dependent mechanism," J Cell Biol. 140(40: 861-871, 1998.
Madjd et al., "Upregulation of MICA on High-Grade Invasive Operable Breast Carcinoma," Cancer Immunity, vol. 7, pp. 1-10 (2007).
Mittendorf et al., "Breast cancer vaccines: promise for the future or pipe dream?" Cancer, 110(8): 1677-1686, 2007.
Miyazaki et al., "The Liposome-Incorporating Cell Wall Skeleton of *Mycobacterium bovis* Bacillus Calmette-Guein can Directly Enhance the Susceptibility of Cancer Cells to Lymphokine-Activated Killer Cells Through Up-Regulation of Natural-Killer Group 2, Member D Ligands," BJU International, pp. 1-7 (2011).
Moingeon et al., "Human natural killer cells and mature T lymphocytes express identical CD3 Zeta subunits as defined by cDNA cloning and sequence analysis", Eur. J. Immunol. 1990 20:1741-1745.
NCBI Accession No. AB055881 [gi:17221621] with Revision History—Dec. 1, 2001.
NCBI Accession No. AF019562 [gi:2905993] with Revision History—Jan. 26, 1999.
NCBI Accession No. AF072845 [gi:5690195].
NCBI Accession No. AF098358 [gi:4139191].
NCBI Accession No. AF133299 [gi:6651064].
NCBI Accession No. AF461157 [gi:18182677].
NCBI Accession No. AF461811 [gi:18182679] Jan. 17, 2002.
NCBI Accession No. AF461812 [gi:18182681].
NCBI Accession No. AJ001383 [gi:3647278] with Revision History—Sep. 22, 1998.
NCBI Accession No. AJ001684 [gi:2980858] with Revision History—Sep. 4, 1998-Nov. 14, 2006.
NCBI Accession No. AJ225109 [gi:4493701] with Revision History—Mar. 15, 1999.
NCBI Accession No. AJ271694 [gi:6900101] with Revision History—Feb. 2, 2000-Nov. 14, 2006.
NCBi Accession No. AJ312373 [gi:14599393] with Revision History—Jul. 3, 2001-Apr. 15, 2005.
NCBI Accession No. BC-30937 {gi:24980984] with Revision History—Jun. 25, 2004-Jul. 15, 2006.
NCBI Accession No. M33195 [gi:182487] with Revision History—Oct. 2, 1992-Apr. 27, 1993.
NCBI Accession No. NM_016509 with Revision History—Mar. 2, 2006-Nov. 18, 2006.
NCBI Accession No. NM_001781 [gi: 4502680] with Revision History—Mar. 30, 2006-Nov. 17, 2006.
NCBI Accession No. NM_001782 [gi:4502682] with Revision History—Aug. 13, 2006-Mar. 11, 2007.
NCBI Accession No. NM_002262 [gi:7669497] with Revision History—Feb. 5, 2006-Nov. 17, 2006.
NCBI Accession No. NM_002543 [gi:37595562] with Revision History—Aug. 13, 2006-Feb. 18, 2007.
NCBI Accession No. NM_007334 [gi:7669498] with Revision History—Feb. 5, 2006-Nov. 17, 2006.
NCBI Accession No. NM_016523 [gi:7705573] with Revision History—Apr. 22, 2005-Feb. 27, 2007.
NCBI Accession No. NM_198053 [gi:37595564] with Revision History—Oct. 15, 2006-Jan. 14, 2007.
NCBI Accession No. U11276 [gi:538270] with Revision History—Sep. 16, 1994-Sep. 23. 1994.

(56) References Cited

OTHER PUBLICATIONS

Nowbakht et al., "Ligands for Natural Killer Cell-Activating Receptors are Expressed Upon the Maturation of Normal Myelomonocytic Cells but at Low Levels in Acute Myeloid Leukemias," Blood, vol. 105, pp. 3615-3622 (2005).
Nuckel et al., "The Prognostic Significance of Soluble NKG2D Ligands in B-Cell Chronic Lymphocytic Leukemia," Leukemia, vol. 24, pp. 1152-1159 (2010).
Oelke et al., "Ex vivo induction and expansion of antigen-specific cytotoxic T cells by HLA-Ig-coated artificial antigen-presenting cells", Nature Medicine 2003 9(5):619-624.
Reilly, R. Todd, "Proper Costimulation of Tumor-Reactive T Lymphocytes May Provide a Key to Unlock Their Antitumor Activity", Cancer Biology & Therapy 2003 2(5):587-588.
Rosen, et al. "A Structural basis for the association of DAP12 with mouse, but not human, NKG2D," J Immunol. Aug. 15, 2004;173(4):2470-8.
Salih et al., "Functional Expression and Release of Ligands for the Activating Immunoreceptor NKG2D in Leukemia," Blood, vol. 102, pp. 1389-1396 (2003).
Sconocchia et al., "The Antileukemia Effect of HLA-Matched NK and NK-T Cells in Chronic Myelogenous Leukemia Involves NKG2D-Target-Cell Interactions," Blood, vol. 106, pp. 3666-3672 (2005).
Stancovski et al., "Targeting of T Lymphocytes to Neu/HER2-Expressing Cells Using Chimeric Single Chain Fv Receptors", J. Immunol 1993 151(11):6577-6582.
Stevens et al., "Generation of Tumor-Specific CTLs from Melanoma Patients by Using Peripheral Blood Stimulated with Allogeneic Melanoma Tumor Cell Lines", J. Immunol 1995 154:762-771.
Suzuki et al., "The Anticancer Effect of γδ T-Cells is Enhanced by Valproic Acid-Induced Up-Regulation of NKG2D Ligands," Anticancer Research, vol. 30, pp. 4509-4514 (2010).
Textor et al., "Activating NK Cell Receptor Ligands are Differentially Expressed During Progression to Cervical Cancer," International Journal of Cancer, vol. 123, pp. 2343-2353 (2008).
Thomis et al., "A Fas-based suicide switch in human T cells for the treatment of graft-versus-host disease", Blood 2001 97(5):1249-1257.
Ulmer et al., "Gene-based vaccines: recent technical and clinical advances," Trends Mol Med. 12(5): 216-222, 2006.
Vetter et al., "Expression of Stress-Induced MHC Class I Related Chain Molecules on Human Melanoma," The Journal of Investigative Dermatology, vol. 118, No. 4, (2002).
Wilson, et al. "DAP12 and KAP10 (DAP10)-novel transmembrane adapter proteins of the CD3zeta family," Immunol Res. 2000;22(1):21-42.
Wu et al., "Prevalent Expression of the Immunostimulatory MHC Class I Chain-Related Molecule is Counteracted by Shedding in a Prostate Cancer," The Journal of Clinical Investigation, vol. 114, No. 4 (2004).
Wu et al., "An activating immunoreceptor complex formed by NKG2D and DAP10," Science, 285: 730-732, 1999.
Xu et al., "Clinicopathological Significance of Major Histocompatibility Complex Class I-Related Chain A and B Expression in Thyroid Cancer," The Journal of Clinical Endocrinology and Metabolism, vol. 91, No. 7, pp. 2704-2712 (2006).
Zhang et al., "Chimeric NK-receptor-bearing T cells mediate antitumor immunotherapy", Blood 2005 106(5):1544-1551.
Carbone, et al. "HLA class I, NKG2D, and natural cytotoxicity receptors regulate multiple myeloma cell recognition by natural killer cells," Blood. Jan. 1, 2005;105(1):251-8.
This application is a Division of, U.S. Appl. No. 17/748,683, filed May 19, 2022, Pending.
Is a Division of, U.S. Appl. No. 16/458,740, filed Jul. 1, 2019, Patented, U.S. Pat. No. 11,339,199.
Is a Division of, U.S. Appl. No. 14/600,799, filed Jan. 20, 2015, Patented, U.S. Pat. No. 10,336,804.
Is a continuation of, U.S. Appl. No. 12/407,440, filed Mar. 19, 2009, Abandoned.
Is a Continuation-in-part of, U.S. Appl. No. 11/575,878, filed Apr. 19, 2007, Patented, U.S. Pat. No. 7,994,298.

```
   1 tgaggacata tctaaatttt ctagttttat agaaggcttt tatccacaag aatcaagatc
  61 ttccctctct gagcaggaat cctttgtgca ttgaagactt tagattcctc tctgcggtag
 121 acgtgcactt ataagtattt gatggggtgg attcgtggtc ggaggtctcg acacagctgg
 181 gagatgagtg aatttcataa ttataacttg gatctgaaga agagtgattt ttcaacacga
 241 tggcaaaagc aaagatgtcc agtagtcaaa agcaaatgta gagaaaatgc atctccattt
 301 tttttctgct gcttcatcgc tgtagccatg ggaatccgtt tcattattat ggtagcaata
 361 tggagtgctg tattcctaaa ctcattattc aaccagaag ttcaaattcc cttgaccgaa
 421 agttactgtg cccatgtcc taaaaactgg atatgttaca aaataactg ctaccaattt
 481 tttgatgaga gtaaaaactg gtatgagagc caggcttctt gtatgtctca aaatgccagc
 541 cttctgaaag tatacagcaa agaggaccag gatttactta aactggtgaa gtcatatcat
 601 tggatgggac tagtacacat tccaacaaat ggatcttggc agtgggaaga tggctccatt
 661 ctctcaccca acctactaac aataattgaa atgcagaagg gagactgtgc actctatgcc
 721 tcgagcttta aaggctatat agaaaactgt tcaactccaa atacatacat ctgcatgcaa
 781 aggactgtgt aaagatgatc aaccatctca ataaagcca ggaacagaga agagattaca
 841 ccagcggtaa cactgccaac cgagactaaa ggaaacaaac aaaaacagga caaaatgacc
 901 aaagactgtc agatttctta gactccacag gaccaaacca tagaacaatt tcactgcaaa
 961 catgcatgat tctccaagac aaaagaagag agatcctaaa ggcaattcag atatccccaa
1021 ggctgcctct cccaccacaa gcccagagtg gatgggctgg gggagggtg ctgtttaat
1081 ttctaaaggt aggaccaaca cccagggat cagtgaagga agagaaggcc agcagatcag
1141 tgagagtgca acccccacct ccacaggaaa ttgcctcatg ggcagggcca cagcagagag
1201 acacagcatg ggcagtgcct tccctgcctg tggggtcat gctgccactt ttaatgggtc
1261 ctccacccaa cggggtcagg gaggtggtgc tgccctagtg ggccatgatt atcttaaagg
1321 cattattctc cagccttaag atcttaggac gttttccttg ctatgatttg tacttgcttg
1381 agtcccatga ctgtttctct tcctctcttt cttcctttg gaatagtaat atccatccta
1441 tgtttgtccc actattgtat tttggaagca cataacttgt ttggtttcac aggttcacag
1501 ttaagaagga attttgcctc tgaataaata gaatcttgag tctcatgcaa aaaaaaaaa
1561 aaaaaaaaaa aaaaa (SEQ ID NO:2)
```

FIG. 3A

```
   1 gcagttatca tagagcacag tccctcacat cacacagctg cagagatgag taaacaaaga
  61 ggaaccttct cagaagtgag tctggcccag gacccaaagc ggcagcaaag gaaacctaaa
 121 ggcaataaaa gctccatttc aggaaccgaa caggaaatat tccaagtaga attaaatctt
 181 caaaatcctt ccctgaatca tcaagggatt gataaaatat atgactgcca aggtaaaaca
 241 ttaaatatat cttcaatatt attgttctag gatgtgcagt tgaatgcaga agggtgagga
 301 aagattaggg aatattttgc acttgtgaga atcggagttc ataattggga tctaaaattc
 361 taatatgaaa tcagaagact aattttattc gggcattgtt caactgtaat ctgcggtcca
 421 ctcatggaac attatattta ctgaaaatga aatggtatat tctgagagaa agattactag
 481 agtagatgta gatttagagg ccagagttta tcattatgtt tccctgtgca tgtgggttct
 541 ctagtatgta attctctagt atgtaatcct aatcaactct ctatctcccc tctctcagtg
 601 cctctatttc tctccctgca ggtttactgc cacctccaga gaagctcact gccgaggtcc
 661 taggaatcat ttgcattgtc ctgatggcca ctgtgttaaa aacaatagtt cttattcctt
 721 gtaagcatat tcttgaaaga ttagaaggga acgttttact ttaatgcttg gaagtgcctc
 781 aaaatatttc atactgttga agaatagaac tcttatttta ctgtttcttt caaagatcta
 841 ttacttcatt tattttttata gaaaaagtta attttattaa agattgtccc cattttaaat
 901 aacacacaaa gtttcaaagt aagaaactaa actcattatg gtttatctaa atattacttt
 961 ttataaaaat cattttaatt tttctgttac agtcctggaa cagaacaatt cttccccaaa
1021 tacaagaacc cagaaaagta cattttatt ttcaaagttc tgatattagt acaatttgga
1081 accaaaagta atatggttat tctgaatttt tcacaacata aataacaaaa tcattgtaga
1141 gaacatgtgt ttatttttg tgtgtaatct atatatatgt atatacatac acacacaaag
1201 atattttctg atttcataat tcaaaggcat gctatagaag aaaagtattt agaaaaacaa
1261 attaattttt gaaagtggtt acatcaaata ctacaagaga tggtgaagtt tgtgctaaag
1321 tctttaaaaa tgtttatttc aaaggtctat tactttatat atttttatag aaaaagttaa
1381 ttttattaaa gattctcccc attttaaata acacacaaag tttcaaagta agaaactaaa
1441 ctcgttatgg ttcatctaga tatcagtttt tataaaaatc attttaattt ttctattaca
1501 gtcctggagc agaacaattc ttccccgaat acaagaacgc agaaaggtac attttattt
1561 tcaatgttct gatattagta caatttatat tttgtgtctg ttttaaggca tgtaaaagaa
1621 tagtggcatt tttgcagaaa ataagccata aattcagcca taaatatttg taaagaaaga
1681 ttatgaggca gcatttcctt ttctccagtg agtagaaata ctcacttaaa atcattctac
1741 cctctttctc ccaattaaca gaggtttcct actgctgtga gatgatacca aataaataat
1801 tttactattc taaaaaagca gttgtgtatc agcgatgttc aacacatgtg tagagtgtat
1861 ttttgtttgt tcatttgctt tatatgggaa cacaattagg gaggagaggc taaccccttgt
1921 ctgtgcatgt gtgtatgact gactcagtta ttaaaaatat acatttataa gcctgtaagg
1981 atgcgtaaat atgttaagca catatatgtt tatactgttg aaatatgtga actaattttc
2041 atttttaaaa attcatattg gtctaaatag taattcatat ctttattagc acgtcattgt
2101 ggccattgtc ctgaggagtg gattacatat tccaacagtt gttattacat tggtaaggaa
2161 agaagaactt gggaagagag tttgctggcc tgtacttcga agaactccag tctgctttct
2221 atagataatg aagaagaaat ggtaagatgt aaatgtttca aacattttat gaaaagcttc
2281 cttcagtgaa taatacattt gtagaaaaca tccatatgtg tgtacatata tttatctcat
2341 atattttcaa gtgtatgtaa tattcaattg attgacttaa taatgttttt aaagttatat
2401 actgctaatg tacatttatt ttcagttttt gtttttcaag gaaaaccatg cttctataag
2461 tgctttgaat ccacaataaa ttttgctatc taattttatc gggcatgata tcatctggtc
2521 atgcagattg atcacaaagt gaatgaatgc atgtgataca agtcagatca tgaaataaaa
2581 gtttccagct ctagcagttc caccccctgtg tatgccctca tcacttatcc tgactcctct
2641 ccaaaacgca gtcttgactt taatattat aaataatgat tgcctgttct tgaatttatt
2701 tatataaagg gaatcaaaca gtgtgaattt catgtctttt tcaatcctat ctgatatttg
2761 tgcaattcct ccatattatt gcagttatca gtagtatgtt actgttcact gctgtactat
2821 gtacaaagaa cagtaagaat ccattgagtc cttgtctctg gatggggaag tgggtctcat
2881 gccctcaggg acaaagagga ccctaggtgg tttacggtgc actgttagtc atgggtccc
2941 tttgctgatc ctcctcatcc acagccatcc tggtgtctct tggtatgaga aggaagcact
```

FIG. 3B

```
3001 ttctctagct ccatattggt agcaggtctc ctggtagatc atccttgcca gtggcaccag
3061 ccttgcctgg tattgtggag gggactctcc ttcgataccc tcctcctatt gccaggttgg
3121 gtgtagggaa acagcaggcc taggtcacct tcttctgtcg tgtggaggac ttaacatgct
3181 cacttggaca cttggttgat ccctgatgct agggtcccag acaatttcat ctttctcttt
3241 ccacctttca gagttctcca ttgcttttgt ctttcattaa tcccagagtt tatagttgtt
3301 tttagtaggg agtagcagag agagacgagt ctacaccacc tggccaggac ccctgttatt
3361 ccgcaaaaac cgaatcggat aaaaattgag ggcttatcta gttaaagaat ggtgtggtac
3421 ccagaaaacc caatctgtag cttccatgtc atctatttct gaatgacaac ccctcaattc
3481 ccttctaaat ctccaactct gagaaatata gcacaaaaat agattgattt agtcacagta
3541 tctggagaaa tgaatgcaca gtatcaggaa acttattaaa acccttcctg tgtttattct
3601 gttaattgga gtaactatta cattgcaaga attaaaatgt ctttattaac atgagaataa
3661 gaatgaaagt actaagtata aacgttgaag agttcattta ataaaaaat tcaaacattt
3721 atgaaagttt ttggcactgc aaatagtggt tttcaacttt aatatattgt ttttgtaatg
3781 ttttcataat tattatttaa gtgaaaatta tttctttttct tttagaaatt tctggccagc
3841 attttacctt cctcatggat tggtgtgttt cgtaacagca gtcatcatcc atgggtgaca
3901 ataaatggtt tggctttcaa acataagtaa gttcttttgt atggcgctat ataaaaaata
3961 tatataaagg ataaattcag aagaataata tgaataaatt tatgtggaat cattgacatg
4021 aagaaagatg tggaaagtta gtgaaatgtt gatataaata ttttacaata gaccatagta
4081 gtccatatat ttcaaccgct cattggtctg ctagtaacct tcttggttat cagatggacc
4141 aggggtgtcc catctttggc ttctgtgggc cacgttagaa gacgaatagt cttggcccac
4201 acatagaata cactaacact aacgatagct gacgagctaa aaaaaaaaaa aaatcacaga
4261 atgttttaag aaagtttacg tatttgtgtt gggccgcatt caaagctgtc ctgggtcacg
4321 tgcggcccat gggcagcgag ttggacaacc tcgagctgga ctatcaggga actgcagtgc
4381 ttgttttat taaaaagcca cgcttacttt tttacttaag aatatcctca aagcacaata
4441 atagtgctgt tggcatattg ctataatttt tttattacta gttattgttg tcaatctctt
4501 attgtgccta atttataaat taaactttat cacagttatg aatgtgtaga gaaaacataa
4561 tctctctata ggttctgcac tatctgccat tcaggcatc cactggggtc ttgaaacata
4621 tccctcgtgg atgaagaggg actactctgt tgagtgttca gaataatgac tcttactaat
4681 attatgaaaa atttaattac ccttttccat gaaattcttt cttacagta catggaaaat
4741 gctttcgtct catgaatcat ttgcttaaaa tgtaacagaa tatggatttt tctccattac
4801 aggataaaag actcagataa tgctgaactt aactgtgcag tgctacaagt aaatcgactt
4861 aaatcagccc agtgtggatc ttcaatgata tatcattgta agcataagct ttagaagtaa
4921 agcatttgcg tttacagtgc atcagataca ttttatattt cttaaaatag aaatatttatg
4981 attgcataaa tctgaaaatg aattatgtta tttgctctaa tacaaaaatt ctaaatcaat
5041 tattgaaata ggatgcacac aattactaaa gtacagacat cctagcattt gtgtcgggct
5101 cattttgctc aacatggtat ttgtggtttt cagccttcct aaaagttgca tgttatgtga
5161 gtcagcttat aggaagtacc aagaacagtc aaacccatgg agacagaaag tagaatagtg
5221 gttgccaatg tctcagggag gttgaaatag gagatgacca ctaattgata gaacgtttct
5281 ttgtgtcgtg atgaaaactt tctaaatttc agtaatggtg atggttgtaa ctttgcgaat
5341 atactaaaca tcattgattt ttaatcattt taagtgcatg aaatgtatgc tttgtacatg
5401 acacttcaat aaagctatcc agaaaaaaaa aagcctctga tgggattgtt tatgactgca
5461 tttatctcta aagtaatttt aaagattagc ttctttataa tattgacttt tctaatcagt
5521 ataaagtgtt tccttcaatg tactgtgtta tctttaattt ctctctcttg tatttgtat
5581 tttgggggat tgaagtcata cagaaatgta ggtatttttac atttatgctt ttgtaaatgg
5641 catcctgatt ctaaaattcc cttagtaat ttttgttgtt ataaatagaa atacaactga
5701 tgtctgcatt ttgatttat atctacttat tccactgatt ttatatattt aaatctatta
5761 tgtcaactat tgatttattt ctgggtgttc tatataacga gcaatttat ctgcaaatga
5821 tcacactttt atttttttta atccatgtgc tataacttag ttttattttc atttattttc
5881 actggctaag gttttatacc catagttgaa tagaaggcac aatcaaagtt ctttgtggat
5941 catatgcatc attttctggt tttggcaaaa aatacttcaa catgttatac atatttaaaa
6001 agcttggtgt ttttgcatc ctatctttct catatcgaag cagttttata atcctatttt
6061 ctaatagatt ttatcaattg taacaatttt tattaatt (SEQ ID NO:3)
```

*FIG. 3C*

```
   1 aattcccagc cctggagctg gcattccagt gggaggccac tctcagtttc acttggtgac
  61 ctttcacagc actgaccatg ttggccctat ttctcccctg cttgcttgct tttctatttt
 121 attttattat tacatttta ttgttagaga gagggtctca ttctgtcgcc caggctggag
 181 tgcagtggca aagtggtgag atctcggctc actgcaacct ccacttgcct cagtctccca
 241 agtagctggg attacaggag cctgacacca tgcccgggta attttgtat tttgtagag
 301 acggggtttc accatattgg cttgaactcc tgatctcagg tgatccccc accttggcct
 361 cccaaagtgc tgggattaca ggcatgagcc actgcggtgg cctctcccct gctttcaaga
 421 tgccatgctc tcagggtcc cctccctctt tctccatttc cctggcaaag ttcctcctct
 481 tcccccattc agtgtgtgtt gtgataggg cagaatcctg tctgcactca cttccttggt
 541 gatctcaccc agtcttgtgg ctttaagtac catccataag ccatcaaccc caaatttac
 601 atctccagac cagccttatc ccctgaactc ctaaatgcag tgaggttatt cagcatctcc
 661 acaggagat tgtcaggcat ttccaaccct gtatgcccaa acctcgtcac tttccccgca
 721 aacccacttc cctacctttc atctctgcca gcagacactc ccatcttctc agcgtttcat
 781 gccagaaggc ttggctgtct aggatccctc tcaaacacac ccacattcat ttaatcagca
 841 aattttcttg gccctacctc caaaatattt ccagatctcc ctagcctgca cacccttgcc
 901 acctgtcatt cccacttgga ccaggccagc agcctccctg gtctctctga ccctcccct
 961 gagttcgttc accaaaggca gtaacggaga cacccctca acacacacag aagcagatg
1021 gccttgacac cagcagggtg acatccgcta ttgctacttc tctgctcccc cacagttcct
1081 ctggacttct ctggaccaca gtcctctgcc agaccctgc cagaccccag tccaccatga
1141 tccatctggg tcacatcctc ttcctgcttt gctcccagg tgaagccagt ggttacaggg
1201 gatggtaggc agagcgtttg tgagatgggt gcttgggtga cgtctgcagg gacgggtgat
1261 gaaagtgggg ttcttctccc tgcacccctt cccttctggg agatccattc tgcttcaggg
1321 cctgggtcct tgggggcgga agggggtgag acagggagtt ctggagggc tgcctgttag
1381 cgtcccttc tcatggctgg gtctctgctg ccacttccaa tttcttgtca ctctccatgt
1441 ctctgggagt cccttccca tgtggtcctg ttccatctct ccagcctgga gattacttct
1501 caggacacta cctttccttc tctacaccct attttttggt ttgtttattt tgagatgggg
1561 tcttgctctg ttgtccaggc tggagtgcag tggcacaatc acggctcacg gcagccttga
1621 cttcctgggc tcaggtgatc ctcccagctc agcctcccga gtaactggga ttacaggtgt
1681 gaaccaacac ttccagctaa ttttgtatt tcttgtagag acgaggtctc actatgttgc
1741 ccaggctggt ctcgaactcc tgggctcaag cgatcttcct gcctcggcct cccaaagtgc
1801 tgggatgaca ggcgtgagcc acggtgccag gctgagcatt ctgttttgtg gaccttctct
1861 ccaccctcat ccaccttctt tctctttcca cagtggctgc agctcagacg actccaggag
1921 agagatcatc actccctgcc ttttaccctg gcacttcagg tatcacttcc accccagaag
1981 cttggccaga ggctcccaga acacccagt ggttctccag gtcaccatcc cacctcccgt
2041 ccccaaatca gaggatccgt gtccttctcc gagtcccaga atcagcgacc ccagcctgt
2101 gttcaggagc acccgtgtg cccgccgcac agcccgagg gtcctgggac accccagcct
2161 ctctgcatct gtctcccgtt tcattcccca agcgcaactc caaggaacct gggacccgcc
2221 ccctcgcagg ggacttcctc tctgcctgtg gccaaagcac agcccagga cgcagagctt
2281 gagttgtctc cctgttccgg cccccactct ccaggctctt gttccggatg tgggtccctc
2341 tctctgccgc tcctggcagg cctcgtggct gctgatgcgg tggcatcgct gctcatcgtg
2401 ggggcggtgt tcctgtgcgc acgcccacgc cgcagccccg cccaaggtga gggcggagat
2461 gggcggggcc tggaaggtgt atagtgtccc tagggagggg gtcccaggga ggggcccctt
2521 gggaagccc tggaggaggt gctggggaaa ccctggggga ggtgcctggg gaaccctg
2581 aggaaacccc tgaagcaggg ggtccccagg gaagtggaga tatgggtggt caagcttcat
2641 gctttctctc ccctatcccc agaagatggc aaagtctaca tcaacatgcc aggcaggggc
2701 tgaccctcct gcagcttgga cctttgactt ctgaccctct catcctggat ggtgtgtggt
2761 ggcacaggaa ccccgcccc aactttgga ttgtaataaa acaattgaaa cacctgtagt
2821 cgtattcttt ctcaaagaac cccagagttc ccaaagcctc cctcccatga actgtttctg
2881 gatccaaggc cccctcagaa ccccacatg tccccatccc atcagcccaa ggatctggca
2941 taatgttttt gtgcttcatg tttattttag gagagtattg gggagcggtc tggtctctca
(SEQ ID NO:4)
```

FIG. 4A

```
  1 ccacgcgtcc gcgctgcgcc acatcccacc ggcccttaca ctgtggtgtc cagcagcatc
 61 cggcttcatg gggggacttg aaccctgcag caggctcctg ctcctgcctc tcctgctggc
121 tgtaagtggt ctccgtcctg tccaggccca ggcccagagc gattgcagtt gctctacggt
181 gagcccgggc gtgctggcag ggatcgtgat gggagacctg gtgctgacag tgctcattgc
241 cctggccgtg tacttcctgg gccggctggt ccctcggggg cgaggggctg cggaggcagc
301 gacccggaaa cagcgtatca ctgagaccga gtcgccttat caggagctcc agggtcagag
361 gtcggatgtc tacagcgacc tcaacacaca gaggccgtat tacaaatgag cccgaatcat
421 gacagtcagc aacatgatac ctggatccag ccattcctga agcccaccct gcacctcatt
481 ccaactccta ccgcgataca gacccacaga gtgccatccc tgagagacca gaccgctccc
541 caatactctc ctaaaataaa catgaagcac aaaaaaaaaa aaaaaaaaa aaaaaaaaa
601 aaaa (SEQ ID NO:5)
```

FIG. 4B

```
  1 gtcctccact tcctggggag gtagctgcag aataaaacca gcagagactc cttttctcct
 61 aaccgtcccg gccaccgctg cctcagcctc tgcctcccag cctctttctg agggaaagga
121 caagatgaag tggaaggcgc ttttcaccgc ggccatcctg caggcacagt gccgattac
181 agaggcacag agctttggcc tgctggatcc caaactctgc tacctgctgg atggaatcct
241 cttcatctat ggtgtcattc tcactgcctt gttcctgaga gtgaagttca gcaggagcgc
301 agacgccccc gcgtaccagc agggccagaa ccagctctat aacgagctca atctaggacg
361 aagagaggag tacgatgttt tggacaagag acgtggccgg gaccctgaga tgggggaaa
421 gccgcagaga aggaagaacc ctcaggaagg cctgtacaat gaactgcaga agataagat
481 ggcggaggcc tacagtgaga ttgggatgaa aggcgagcgc cggagggca agggcacga
541 tggcctttac cagggtctca gtacagccac caaggacacc tacgacgccc ttcacatgca
601 ggccctgccc cctcgctaac agccagggga tttcaccact caaaggccag acctgcagac
661 gcccagatta tgagacacag gatgaagcat ttacaacccg gttcactctt ctcagccact
721 gaagtattcc cctttatgta caggatgctt tggttatatt tagctccaaa ccttcacaca
781 cagactgttg tcctgcact ctttaaggga gtgtactccc agggcttacg gccctggcct
841 tgggccctct ggtttgccgg tggtgcaggt agacctgtct cctggcggtt cctcgttctc
901 cctggggagc gggcgcactg cctctcacag ctgagttgtt gagtctgttt tgtaaagtcc
961 ccagagaaag cgcagatgct agcacatgcc ctaatgtctg tatcactctg tgtctgagtg
1021 gcttcactcc tgctgtaaat ttggcttctg ttgtcacctt cacctccttt caaggtaact
1081 gtactgggcc atgttgtgcc tccctggtga gaggccgggg cagaggggca gatggaaagg
1141 agcctaggcc aggtgcaacc agggagctgc aggggcatgg gaaggtgggc gggcagggga
1201 gggtcagcca gggcctgcga gggcagcggg agcctccctg cctcaggcct ctgtgccgca
1261 ccattgaact gtaccatgtg ctacagggc cagaagatga acagactgac cttgatgagc
1321 tgtgcacaaa gtggcataaa aaacatgtgg ttacacagtg tgaataaagt gctgcggagc
1381 aagaggaggc cgttgattca cttcacgctt tcagcgaatg acaaaatcat ctttgtgaag
1441 gcctcgcagg aagacccaac acatgggacc tataactgcc cagcggacag tggcaggaca
1501 ggaaaaaccc gtcaatgtac taggatactg ctgcgtcatt acaggcaca ggccatggat
1561 ggaaaacgct ctctgctctg cttttttct actgttttaa tttatactgg catgctaaag
1621 ccttcctatt ttgcataata aatgcttcag tgaaaaaaaa aaaaaaaaa aaaaaa
(SEQ ID NO:6)
```

FIG. 5A

```
  1 cagaacggcc gatctccagc ccaagatgat tccagcagtg gtcttgctct tactccttt
 61 ggttgaacaa gcagcggccc tgggagagcc tcagctctgc tatatcctgg atgccatcct
121 gtttctgtat ggaattgtcc tcaccctcct ctactgtcga ctgaagatcc aagtgcgaaa
181 ggcagctata accagctatg agaaatcaga tggtgtttac acgggcctga gcaccaggaa
241 ccaggagact tacgagactc tgaagcatga gaaaccacca cagtagcttt agaatagatg
301 cggtcatatt cttctttggc ttctggttct tccagccctc atggttggca tcacatatgc
361 ctgcatgcca ttaacaccag ctggccctac ccctataatg atcctgtgtc ctaaattaat
421 atacaccagt ggttcctcct ccctgttaaa gactaatgct cagatgctgt ttacggatat
481 ttatattcta gtctcactct cttgtcccac ccttcttctc ttccccattc ccaactccag
541 ctaaaatatg ggaagggaga accccaata aaactgccat ggactggact c
(SEQ ID NO:7)
```

FIG. 5B

NUCLEIC ACID CONSTRUCTS ENCODING CHIMERIC NK RECEPTOR, CELLS CONTAINING, AND THERAPEUTIC USE THEREOF

RELATED APPLICATION DISCLOSURE

This application is a divisional of U.S. patent application Ser. No. filed May 19, 2022, which is a divisional of U.S. patent application Ser. No. 16/458,740 filed Jul. 1, 2019 (now U.S. Pat. No. 11,339,199), which is a divisional of U.S. patent application Ser. No. 14/600,799 filed Jan. 20, 2015, (now U.S. Pat. No. 10,336,804), which is a continuation of U.S. patent application Ser. No. 12/407,440 filed Mar. 19, 2009 (now abandoned), which is a Continuation-in-part of U.S. patent application Ser. No. 11/575,878 filed Apr. 19, 2007 (now U.S. Pat. No. 7,994,298), which is a National Stage Entry of international Patent Cooperation Treaty Application No. PCT/US05/31100 filed Aug. 31, 2005, which claims priority to U.S. Provisional Application No. 60/681,782 filed May 17, 2005 and U.S. Provisional Application No. 60/612,836 filed Sep. 24, 2004, each and all of which are incorporated herein by reference in their entireties.

This invention was made in the course of research sponsored by the National Cancer Institute (Grant No. CA 101748). The U.S. government has certain rights in this invention.

This application includes as part of its disclosure a biological sequence listing contained in a filed named "1148307o000209.txt" having a size of 23,079 bytes that was created Jun. 15, 2022, which is hereby incorporated by reference in its entirety.

BACKGROUND OF THE INVENTION

T cells, especially cytotoxic T cells, play important roles in anti-tumor immunity (Rossing and Brenner (2004) *Mol. Ther.* 10:5-18). Adoptive transfer of tumor-specific T cells into patients provides a means to treat cancer (Sadelain, et al. (2003) *Nat. Rev. Cancer* 3:35-45). However, the traditional approaches for obtaining large numbers of tumor-specific T cells are time-consuming, laborious and sometimes difficult because the average frequency of antigen-specific T cells in periphery is extremely low (Rosenberg (2001) *Nature* 411:380-384; Ho, et al. (2003) *Cancer Cell* 3:431-437; Crowley, et al. (1990) *Cancer Res.* 50:492-498). In addition, isolation and expansion of T cells that retain their antigen specificity and function can also be a challenging task (Sadelain, et al. (2003) *supra*) Genetic modification of primary T cells with tumor-specific immunoreceptors, such as full-length T cell receptors or chimeric T cell receptor molecules can be used for redirecting T cells against tumor cells (Stevens, et al. (1995) *J. Immunol.* 154:762-771; Oelke, et al. (2003) *Nat. Med.* 9:619-624; Stancovski, et al. (1993) *J. Immunol.* 151:6577-6582; Clay, et al. (1999) *J. Immunol.* 163:507-153). This strategy avoids the limitation of low frequency of antigen-specific T cells, allowing for facilitated expansion of tumor-specific T cells to therapeutic doses.

Natural killer (NK) cells are innate effector cells serving as a first line of defense against certain viral infections and tumors (Biron, et al. (1999) *Annu. Rev. Immunol.* 17:189-220; Trinchieri (1989) *Adv. Immunol.* 47:187-376). They have also been implicated in the rejection of allogeneic bone marrow transplants (Lanier (1995) *Curr. Opin. Immunol.* 7:626-631; Yu, et al. (1992) *Annu. Rev. Immunol.* 10:189-214). Innate effector cells recognize and eliminate their targets with fast kinetics, without prior sensitization. Therefore, NK cells need to sense if cells are transformed, infected, or stressed to discriminate between abnormal and healthy tissues. According to the missing self phenomenon (Karre, et al. (1986) *Nature* (London) 319:675-678), NK cells accomplish this by looking for and eliminating cells with aberrant major histocompatibility complex (MHC) class I expression; a concept validated by showing that NK cells are responsible for the rejection of the MHC class I-deficient lymphoma cell line RMA-S, but not its parental MHC class I-positive line RMA.

Inhibitory receptors specific for MHC class I molecules have been identified in mice and humans. The human killer cell Ig-like receptors (KIR) recognize HLA-A, —B, or —C; the murine Ly49 receptors recognize H-2K or H-2D; and the mouse and human CD94/NKG2 receptors are specific for $Qa1^b$ or HLA-E, respectively (Long (1999) *Annu. Rev. Immunol.* 17:875-904; Lanier (1998) *Annu. Rev. Immunol.* 16:359-393; Vance, et al. (1998) *J. Exp. Med.* 188:1841-1848).

Activating NK cell receptors specific for classic MHC class I molecules, nonclassic MHC class I molecules or MHC class I-related molecules have been described (Bakker, et al. (2000) *Hum. Immunol.* 61:18-27). One such receptor is NKG2D (natural killer cell group 2D) which is a C-type lectin-like receptor expressed on NK cells, $\gamma\delta$—TcR$^+$ T cells, and CD8+$\alpha\beta$-TcR$^+$ T cells (Bauer, et al. (1999) *Science* 285:727-730). NKG2D is associated with the transmembrane adapter protein DAP10 (Wu, et al. (1999) *Science* 285:730-732), whose cytoplasmic domain binds to the p85 subunit of the PI-3 kinase.

In humans, two families of ligands for NKG2D have been described (Bahram (2000) *Adv. Immunol.* 76:1-60; Cerwenka and Lanier (2001) *Immunol. Rev.* 181:158-169). NKG2D binds to the polymorphic MHC class I chain-related molecules (MIC)-A and MICB (Bauer, et al. (1999) *supra*). These are expressed on many human tumor cell lines, on several freshly isolated tumor specimens, and at low levels on gut epithelium (Groh, et al. (1999) *Proc. Natl. Acad. Sci. USA* 96:6879-6884). NKG2D also binds to another family of ligands designated the UL binding proteins (ULBP)-1, -2, and -3 molecules (Cosman, et al. (2001) *Immunity* 14:123-133; Kubin, et al. (2001) *Eur. J. Immunol.* 31:1428-1437). Although similar to class I MHC molecules in their $\alpha 1$ and $\alpha 2$ domains, the genes encoding these proteins are not localized within the MHC. Like MIC (Groh, et al. (1996) *supra*), the ULBP molecules do not associate with $\beta_2$-microglobulin or bind peptides. The known murine NKG2D-binding repertoire encompasses the retinoic acid early inducible-1 gene products (RAE-1) and the related H60 minor histocompatibility antigen (Cerwenka, et al. (2000) *Immunity* 12:721-727; Diefenbach, et al. (2000) *Nat. Immunol.* 1:119-126). RAE-1 and H60 were identified as ligands for mouse NKG2D by expression cloning these cDNA from a mouse transformed lung cell line (Cerwenka, et al. (2000) *supra*). Transcripts of RAE-1 are rare in adult tissues but abundant in the embryo and on many mouse tumor cell lines, indicating that these are oncofetal antigens.

Recombinant receptors containing an intracellular domain for activating T cells and an extracellular antigen-binding domain, which is typically a single-chain fragment of a monoclonal antibody and is specific for a tumor-specific antigen, are known in the art for targeting tumors for destruction. See, e.g., U.S. Pat. No. 6,410,319.

Baba et al. ((2000) *Hum. Immunol.* 61:1202-18) teach KIR2DL1-CD3 zeta chain chimeric proteins. Further, WO 02/068615 suggests fusion proteins of NKG2D containing the external domain of NKG2D with a distinct DAP10 interacting domain or with cytoplasmic domains derived from other signaling molecules, for example CD28, for use in engineering cells that respond to NKG2D ligands and potentially create a system with enhanced signaling capabilities.

U.S. Pat. No. 5,359,046 discloses a chimeric DNA sequence encoding a membrane bound protein, wherein the chimeric DNA comprises a DNA sequence encoding a signal sequence which directs the membrane bound protein to the surface membrane; a DNA sequence encoding a non-MHC restricted extracellular binding domain of a surface membrane protein selected from the group consisting of CD4, CD8, IgG and single-chain antibody that binds specifically to at least one ligand, wherein said ligand is a protein on the surface of a cell or a viral protein; a transmembrane domain from a protein selected from the group consisting of CD4, CD8, IgG, single-chain antibody, the CD3 zeta chain, the CD3 gamma chain, the CD3 delta chain and the CD3 epsilon chain; and a cytoplasmic signal-transducing domain of a protein that activates an intracellular messenger system selected from the group consisting of the CD3 zeta chain, the CD3 gamma chain, the CD3 delta chain and the CD3 epsilon chain, wherein the extracellular domain and cytoplasmic domain are not naturally joined together and the cytoplasmic domain is not naturally joined to an extracellular ligand-binding domain, and when the chimeric DNA is expressed as a membrane bound protein in a selected host cell under conditions suitable for expression, the membrane bound protein initiates signaling in the host cell.

SUMMARY OF THE INVENTION

The present invention is a nucleic acid construct for expressing a chimeric receptor to reduce or eliminate a tumor. The nucleic acid construct contains a first nucleic acid sequence encoding a promoter operably linked to a second nucleic acid sequence encoding a chimeric receptor protein comprising a C-type lectin-like natural killer cell receptor, or a protein associated therewith, fused to an immune signaling receptor having an immunoreceptor tyrosine-based activation motif of SEQ ID NO:1. The invention also embraces a vector and an isolated host cell harboring the nucleic acid construct and a nucleic acid construct further including a suicide gene.

The present invention also embraces methods for reducing or eliminating tumors and decreasing the regulatory T cell population. These methods involve transducing an isolated T cell with a nucleic acid construct containing a first nucleic acid sequence encoding a promoter operably linked to a second nucleic acid sequence encoding a chimeric receptor protein comprising a C-type lectin-like natural killer cell receptor, or a protein associated therewith, fused to an immune signaling receptor having an immunoreceptor tyrosine-based activation motif of SEQ ID NO:1 so that the chimeric receptor is expressed on the surface of the T cell. The transduced T cell is subsequently injected into a subject in need of treatment thereby decreasing the regulatory T cell population in the subject and reducing or eliminating tumors.

DETAILED DESCRIPTION OF THE INVENTION

Figure 1:
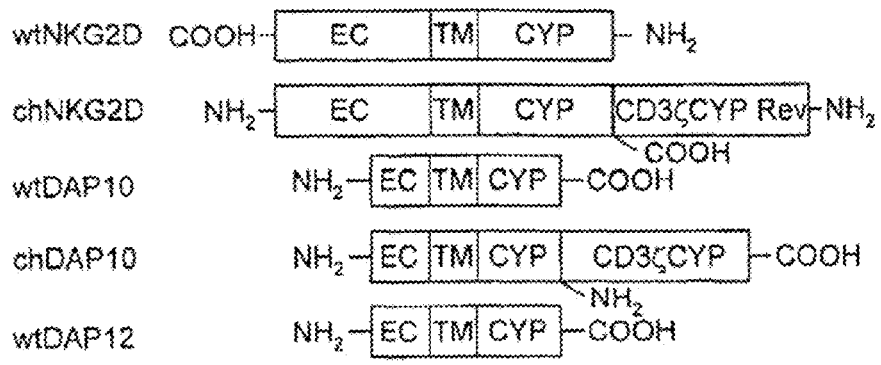
FIG. 1 illustrates chimeric NK receptors exemplified herein. Extracellular (EC), transmembrane (TM), and cytoplasmic (Cyp) portions are indicated. Wild-type (WT) and chimeric (CH) forms of the receptors are indicated, wherein $NH_2$ denotes the N-terminus and CCOH denotes the C-terminus.
Figure 2A:
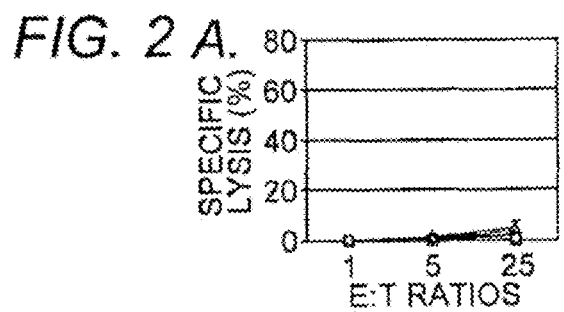
FIGS. 2A to 2E show specific lysis of target cells by gene-modified primary T cells. Effector T cells modified with vector only (shaded diamond), wild-type NKG2D (open square), murine chimeric NKG2D (shaded square), wild-type DAP10 (open triangle), murine chimeric DAP10 (shaded triangle), or wild-type DAP12 (open circle) were co-cultured with target cells RMA (Panel A), RMA/Rae-1β (Panel B), RMA/H60 (Panel C), YAC-1 (Panel. D), or EG7 (Panel E) cells, respectively, at ratios from 1:1 to 25:1 in a 4 hour $^{51}Cr$ release assay. The data are presented as mean±SD and representative of 3 to 5 independent experiments.
Figure 2B:
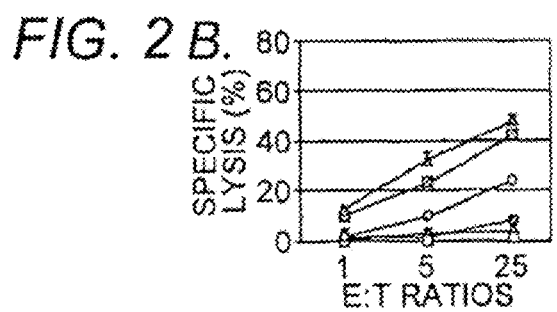
Figure 2C:
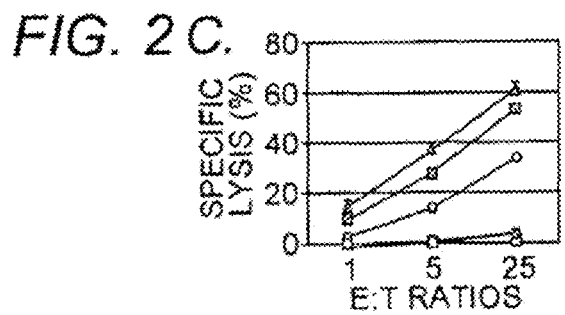
Figure 2D:
Figure 2E:
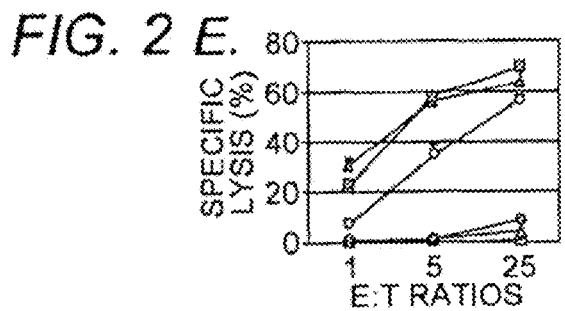

The present invention embraces a chimeric receptor molecule composed of a natural killer cell receptor and an immune signaling receptor expressed on the surface of a T cell to activate killing of a tumor cell. Nucleic acid sequences encoding the chimeric receptor molecule are introduced into T-cells ex vivo and T-cells that express the chimeric receptor molecule are subsequently injected into a subject in need of treatment. In this manner, the chimeric receptor molecules provide a means for the subject's own immune cells to recognize and activate anti-tumor immunity and establish long-term, specific, anti-tumor responses for treating tumors or preventing regrowth of dormant or residual tumor cells. To prevent potential side effects that may occur from uncontrolled inflammation or response against non-tumor tissue, suicide genes are further introduced into the T-cells expressing the chimeric receptor molecule. The suicide gene is activated by administering an agent, specific for the suicide gene, to the patient thereby eliminating all cells expressing the chimeric receptor molecule.

By way of illustration, murine chimeric receptor molecules composed of NKG2D or Dap10 in combination with a N-terminally attached CD3ζ were generated and expressed in murine T-cells. NKG2D is a type II protein, in which the N-terminus is located intracellularly (Raulet (2003) Nat. Rev. Immunol. 3:781-790), whereas the CD3ζ chain is type I protein with the C-terminus in the cytoplasm (Weissman, et al. (1988) Proc. Natl. Acad. Sci. USA 85:9709-9713). To generate a chimeric NKG2D-CD3 fusion protein, an initiation codon ATG was placed ahead of the coding sequence for the cytoplasmic region of the CD3ζ chain (without a stop codon TAA) followed by a wild-type NKG2D gene. Upon expression, the orientation of the CD3ζ portion is reversed inside the cells. The extracellular and transmembrane domains are derived from NKG2D. A second chimeric gene encoding the Dap10 gene followed by a fragment coding for the CD3ζ cytoplasmic domain was also constructed. The structures of the chimeric and wild-type receptors used are diagrammed in FIG. 1.

To determine whether murine chimeric NKG2D or murine chimeric Dap10 receptors could be expressed in a similar manner as wild-type murine NKG2D or Dap10, a NKG2D gene with an adaptor protein gene (Dap10/Dap12) were co-transfected into Bosc23 cells and NKG2D expression was determined by flow cytometry. To analyze those cells that were transfected, a bicistronic vector with a green fluorescent protein (GFP) gene controlled by an internal ribosome entry site (IRES) was used. NKG2D surface expression was normalized by gating on the GFP+ cell population. Like many NK receptors, such as CD94/NKG2C, Ly49D, and Ly49H, NKG2D needs to be associated with adaptor proteins (i.e., Dap10 and/or Dap12) for surface expression (Raulet (2003) supra; Lanier (2003) Curr. Opin. Immunol. 15:308-314) Packaging cell Bosc23 did not express either NKG2D or Dap10/Dap12, and transfection with only one of the two components did not give rise to surface expression of NKG2D. However, co-transfection of a NKG2D gene along with an adaptor protein gene led to significant membrane expression of NKG2D. Compared with Dap12, Dap10 transfection resulted in higher NKG2D surface expression. Surface expression of NKG2D after association with chimeric Dap10 adaptor was higher than that with wild-type DAP10. Higher surface expression of NKG2D was also observed after transfection with chimeric NKG2D than with wild-type NKG2D genes, especially when pairing with the Dap12 gene (>5-fold increase in MFI).

Concentrated, high-titer, retroviral vectors (ecotropic) were used to infect C57BL/6 spleen cells, and NKG2D surface expression was determined by flow cytometry seven days after retroviral transduction. Genetic modification of T cells with wild-type Dap10, Dap12 and NKG2D did not significantly increase the surface expression of NKG2D (10-20%) compared to vector alone. In contrast, significantly higher NKG2D expression was observed in T cells modified with either chimeric NKG2D (42%) or chimeric Dap10 (64%). In chimeric Dap10-transduced T cells, the surface-expressed NKG2D molecules were only due to endogenous molecules, whereas both endogenous and exogenous NKG2D molecules were responsible for surface expression in chimeric NKG2D-modified T cells. Taken together, these data indicate that chimeric NKG2D and chimeric Dap10 molecules are expressed in a similar manner as the wild-type molecules and that they increase NKG2D expression on T cells.

To assess whether the murine chimeric DAP10 or murine chimeric NKG2D-transduced T cells were capable of recognizing NKG2D ligands, NKG2D ligand-positive tumor cells (RMA/Rae-1β, RMA/H60 and YAC-1) were used as targets for chimeric NKG2D-bearing T cells. Chimeric DAP10 or chimeric NKG2D-transduced T cells produced high amounts of IFN-γ (20-30 ng/mL) after co-culture with RMA/Rae-1β, RMA/H60 or YAC-1 cells (Table 1) but not with RMA cells (no ligands), indicating that these chimeric NKG2D-modified T cells could functionally recognize NKG2D ligand-bearing tumor cells.

TABLE 1

| Construct | IFN-γ (ng/mL ± SD) | | | | |
|---|---|---|---|---|---|
| | Media | RMA | RMA/Rae-1β | RMA/H60 | YAC-1 |
| Vector Only | 0.03 ± 0.03 | 0.09 ± 0.18 | 0.02 ± 0.03 | 0.11 ± 0.63 | 0.84 ± 0.29 |
| Wild-type NKG2D* | 0.01 ± 0.01 | 0.10 ± 0.21 | 0.04 ± 0.06 | 0.05 ± 0.00 | 1.08 ± 1.48 |
| Chimeric NKG2D | 0.07 ± 0.08 | 0.37 ± 0.34 | 4.70 ± 0.78 | 8.40 ± 1.60 | 17.80 ± 4.60 |
| Wild-type DAP10* | 0.01 ± 0.10 | 0.11 ± 0.11 | 0.04 ± 0.03 | 0.09 ± 0.03 | 1.43 ± 1.72 |
| Chimeric DAP10 | 0.49 ± 0.55 | 0.82 ± 0.52 | 7.50 ± 4.40 | 18.60 ± 7.60 | 28.70 ± 8.30 |
| Wild-Type DAP12# | 0.00 ± 0.01 | 0.00 ± 0.01 | 0.53 ± 0.67 | 0.13 ± 0.10 | 0.73 ± 0.09 |

*p = 0.74;
p = 0.56.
Data are representative of 3 experiments.

Similarly, chimeric human NKG2D-bearing CD8+T cells secrete IFN-γ when brought into contact with human tumor cells from breast cancer (MCF-7, T47D), prostate cancer (DU145), pancreatic cancer (Pan-1), and melanoma cancer (A375) (Table 2). T cells were cultured with irradiated tumor cells at a 4:1 ratio for 72 hours and IFN-γ was measured by ELISA. T cells cultured without tumor cells functioned as a media only control which produced no detectable IFN-γ. The specificity of the interaction was evident by comparing chimeric NKG2D transduced T cells to vector only.

TABLE 2

| Construct | IFN-γ (pg/mL ± SD) | | | | |
|---|---|---|---|---|---|
| | T47D | MCF-7 | Panc-1 | DU-145 | A375 |
| Vector Only | 28.9 (±12.5) | 53.5 (±3.6) | 97.2 (±8.0) | 61.4 (±4.2) | 262.4 (±44.2) |
| Wild-type NKG2D* | 35.2 (±30.0) | 43.6 (±9.2) | 115.8 (±89.8) | 84.4 (±47.1) | 200.5 (±79.5) |
| Chimeric NKG2D | 130.3 (±70.4) | 2928.3 (±251.1) | 5028.1 (±407.2) | 4427.9 (±470.1) | 2609.2 (±293.2) |
| Tumor Alone | 23.4 (±26.9) | 17.7 (±8.7) | 26.6 (±7.5) | 27.4 (±10.2) | 11.4 (±17.7) |

In addition, upon NKG2D ligation, chimeric DAP10 or chimeric NKG2D-modified T cells also released significant amounts of proinflammatory chemokines (CCL3 and CCL5), as well as Th1 cytokines, GM-CSF and IL-3, but not Th2 cytokines IL-5 and IL-10. In contrast, wild-type Dap10, Dap12 or NKG2D alone-modified T cells did not show any significant response to the stimulation by RMA/Rae-1β, RMA/H60 or YAC-1 cells. These data demonstrate that the chimeric molecules led to the direct activation of T cells.

The cytotoxic activity of murine chimeric NKG2D-modified splenic T cells against tumor cells was also determined. Chimeric Dap10 or chimeric NKG2D-transduced T cells were able to lyse NKG2D ligand-expressing target cells (RMA/Rae-1β, RMA/H60, EG7 and YAC-1) in vitro (FIG. 2, Panels B-E). The specificity of the interaction was apparent from the absence of lysis of YAC-1, EG7, RMA/Rae-1β and RMA/H60 cells by vector only-transduced T cells, and the lack of lysis of RMA cells by chimeric Dap10 or chimeric NKG2D-modified T cells (FIG. 2, Panel A). Similar to cytokine production, no significant specific lysis of tumor cells was observed by wild-type Dap10 or wild-type NKG2D-modified T cells. T cells transduced with wild-type Dap12 were able to kill target cells that expressed ligands for NKG2D. Activated murine CD8+ T cells express NKG2D (associated with Dap10), so expression of Dap12 would allow the endogenous NKG2D to associate with Dap12 and provide a primary activation signal. It is noteworthy that T cells transduced with Dap12 were three- to five-fold less efficient than T cells transduced with chimeric NK receptors at killing tumor cells. The killing of YAC-1 and EG7 tumor cells demonstrates that chimeric NK receptors provide the T cells with a means to kill tumor cells that express endogenous NKG2D ligands.

These data demonstrated the need for NKG2D ligand expression on the target cells. To investigate the role of the NKG2D receptor, it was determined whether blocking antibodies to NKG2D would diminish cytotoxic activity. Chimeric NKG2D-transduced T cells killed RMA/Rae-1β and EG7 tumor cells and this activity was reduced when anti-NKG2D antibodies were included in the assay. Vector only-transduced T cells were unable to kill the target cells and the activity was not changed with the addition of anti-NKG2D antibodies. While the data indicate that the NKG2D receptor was responsible for the activity in these assays, the chimeric receptors may have, in some way, altered the T cells to kill via their T cell receptor. To address this, the ability of chimeric NKG2D-transduced T cells to kill RMA/Rae-1β tumor cells was examined. RMA-S cells are deficient in TAP genes and express very low levels of MHC class I molecules on the cell surface and no MHC class II molecules (Aldrich, et al. (1992) *J. Immunol.* 149: 3773-3777). Chimeric NKG2D-bearing T cells killed RMA/Rae-1p tumor cells but not RMA-S cells. Vector-transduced T cells did not kill either RMA-S cell line. Thus, these data indicate that chimeric NKG2D functions via direct NKG2D recognition of its ligand on target cells.

Having shown that chNKG2D-modified T cells could react against NKG2D ligand-positive tumor cells in vitro, the therapeutic potential of chimeric NKG2D-modified T lymphocytes was determined in vivo. Chimeric NKG2D-bearing T cells ($10^6$) were co-injected with RMA/Rae-1p tumor cells ($10^5$) subcutaneously to C57BL/6 mice. T cells transduced with the chimeric NKG2D construct significantly ($P<0.05$ at days 5-15) inhibited the growth of RMA/Rae-1 tumors compared with vector-transduced T cells or tumor alone (Table 3). Approximately 36% (4/11) of chimeric NKG2D-bearing T cell-treated mice were tumor-free after 30 days. Chimeric NKG2D-bearing T cells did not show any significant inhibition effects on the growth of wild-type RMA cells, indicating that inhibition of RMA/Rae-1β tumor growth by chimeric NKG2D T cells was mediated by chimeric NKG2D-Rae-1β engagement.

TABLE 3

| | Tumor Area (Mean $mm^2$ ± SEM) | | |
|---|---|---|---|
| Day | T Cells transduced with chimeric NKG2D + RMA/Rae-1β | T cells transduced with vector only + RMA/Rae-1β | RMA/Rae-1β |
| 0 | 0.00 ± 0.00 | 0.00 ± 0.00 | 0.00 ± 0.00 |
| 5 | 0.00 ± 0.00 | 16.14 ± 2.86 | 6.79 ± 1.47 |
| 7 | 3.10 ± 1.40 | 38.45 ± 3.79 | 28.69 ± 5.49 |
| 9 | 8.11 ± 3.09 | 57.40 ± 6.43 | 42.22 ± 6.38 |
| 11 | 11.84 ± 5.24 | 90.31 ± 11.64 | 60.60 ± 12.10 |
| 13 | 14.73 ± 7.24 | 127.30 ± 16.85 | 82.67 ± 19.44 |
| 15 | 20.60 ± 8.32 | N. D. | 110.51 ± 29.07 |

Results are a summary of three experiments.

In a second and more stringent model, transduced T cells ($10^7$) were adoptively transferred i.v. into B6 mice one day before s.c. tumor inoculation in the right flank. These chimeric NKG2D-bearing T cells significantly ($P<0.05$ at days 9-17) suppressed the growth of RMA/Rae-1β tumors (s.c.) compared with control vector-modified T cells (Table 4). As for the toxicity of treatment with chimeric NKG2D-modified T cells, the animals treated with chimeric NKG2D-bearing T cells did not show any overt evidence of inflammatory damage (i.e., ruffled hair, hunchback or diarrhea, etc.) indicating there was no overt toxicity.

TABLE 4

| | Tumor Area (Mean $mm^2$ ± SEM) | |
|---|---|---|
| Day | T Cells transduced with chimeric NKG2D | Control T cells with Vector Only |
| 5 | 3.06 ± 1.97 | 4.41 ± 2.20 |
| 7 | 12.14 ± 3.06 | 17.81 ± 1.75 |
| 9 | 13.94 ± 2.85 | 30.58 ± 3.87 |
| 11 | 25.92 ± 4.77 | 45.13 ± 3.27 |
| 13 | 32.11 ± 5.84 | 64.83 ± 10.45 |
| 15 | 34.39 ± 9.77 | 80.72 ± 13.34 |
| 17 | 37.81 ± 11.68 | 96.30 ± 14.15 |

Results are a summary of three experiments.

Because the immune system can select for tumor variants, the most effective immunotherapies for cancer are likely going to be those that induce immunity against multiple tumor antigens. Thus, it was tested whether treatment with chimeric NKG2D-bearing T cells could induce host immunity against wild-type tumor cells. Mice that were treated with chimeric NKG2D-bearing T cells and RMA/Rae-1β tumor cells, and were tumor-free after 30 days, were challenged with RMA tumor cells. These tumor-free mice were resistant to a subsequent challenge of wild-type RMA cells ($10^4$), whereas all control naïve mice had aggressive tumors (tumor area: ~100 $mm^2$) after 2 weeks (Table 5). This observation indicates that adoptive transfer of chimeric NKG2D-bearing T cells allows hosts to generate T cell memory.

TABLE 5

| | Tumor Area (Mean $mm^2$ ± SEM) | |
|---|---|---|
| Day | Mice treated with T Cells transduced with chimeric NKG2D + RMA/Rae-1β | Naïve Mice |
| 5 | 0.00 ± 0.00 | 1.33 ± 2.31 |
| 7 | 0.00 ± 0.00 | 11.65 ± 10.20 |
| 9 | 0.00 ± 0.00 | 38.75 ± 8.84 |
| 11 | 0.00 ± 0.00 | 60.17 ± 6.10 |
| 13 | 0.00 ± 0.00 | 91.10 ± 5.59 |

TABLE 5-continued

| | Tumor Area (Mean mm$^2$ ± SEM) | |
|---|---|---|
| Day | Mice treated with T Cells transduced with chimeric NKG2D + RMA/Rae-1β | Naïve Mice |
| 15 | 0.00 ± 0.00 | 102.81 ± 17.94 |
| 19 | 0.00 ± 0.00 | 146.71 ± 45.72 |

Results are a summary of three experiments.

In similar experiments, human chimeric receptor molecules composed of NKG2D or Dap10 in combination with a N-terminally attached CD3ζ were generated and expressed in Bosc23 cells. Surface expression of NKG2D was not observed when either human Dap10 or human chimeric NKG2D were transfected alone. However, co-transfection of a human chimeric NKG2D or human chimeric NKG2D-GFP gene along with a wild-type human DAP10 gene or mouse DAP10-GFP construct led to significant membrane expression of NKG2D.

Binding of a human NKG2D fusion protein, composed of NKG2D with an N-terminally attached murine IgG1 Fc portion, to human NKG2D ligand on various tumor cell lines was assessed. Human NKG2D ligand was found to be present on Jurkat (T lymphocyte origin), RPMI8866 (B cell origin), K562 (erythroid origin), Daubi (B cell origin), and U937 (monocyte origin) tumor cell lines. Therefore, like the mouse chimeras, a human chimeric NKG2D construct can functionally recognize NKG2D ligand-bearing tumor cells.

The cytotoxic activity of human chimeric NKG2D-modified T cells against tumor cells was also determined. Human chimeric NKG2D-transduced primary human T cells were able to lyse mastocytoma cell line P815 transduced with human MIC-A (P815/MICA-A) in vitro (Table 6). The specificity of the interaction was apparent from the absence of lysis of wild-type P815 tumor cells and the absence of lysis by vector only-transduced T cells.

TABLE 6

| | Tumor Cell Line Specific Lysis (%) | | | | | |
|---|---|---|---|---|---|---|
| | P815/MIC-A | | | P815 | | |
| Effector:Target Ratio | 1 | 5 | 25 | 1 | 5 | 25 |
| Vector Only | 0.0 | 0.0 | 0.6 | 0.0 | −0.6 | 0.0 |
| Human chimeric NKG2D | 5.4 | 17.3 | 35.4 | −2.5 | −0.3 | 1.1 |

Further, blocking of human chimeric NKG2D with an anti-NKG2D antibody prevented killing of K562 and RPMI8866 tumor cells by chimeric NKG2D-transduced human T cells (Table 7). These data demonstrate receptor specificity because a control antibody could not prevent killing.

TABLE 7

| | Tumor Cell Line Specific Lysis (%) | | | | | |
|---|---|---|---|---|---|---|
| | K562 | | | RPMI8866 | | |
| Effector:Target Ratio | 1 | 5 | 25 | 1 | 5 | 25 |
| Vector + control antibody | 0.0 | 0.3 | 2.3 | 0.0 | 1.0 | 0.0 |
| Vector + anti-NKG2D antibody | 0.0 | 0.7 | 2.1 | 0.0 | 1.0 | 1.3 |
| Human chimeric NKG2D + control antibody | 3.1 | 17.6 | 53.8 | 9.3 | 27.4 | 41.6 |
| Human chimeric NKG2D + anti-NKG2D antibody | 1.6 | 10.1 | 27.0 | 1.0 | 2.5 | 7.5 |

Similar to the mouse studies, human chimeric NKG2D-transduced T cells produced high amounts of IFN-γ (~150-2250 pg/mL) after a 24 hour co-culture with tumor cells that express ligands for NKG2D (i.e., Jurkat, RPMI8866, K652, ECC-01 and P815/MIC-A tumor cells) compared with tumor cells that do not express NKG2D ligands (P815) or T cells incubated alone (Table 8). Vector only-transduced T cells did not produce IFN-γ, except against RPMI8866, indicating another ligand on this cell type for these activated T cells; however, IFN-γ production was almost 10-times as high with the human chimeric NKG2D-bearing T cells. Tumor cells alone produce no detectable IFN-γ.

TABLE 8

| | IFN-γ (Mean pg/mL ± SD) | | |
|---|---|---|---|
| Tumor cell Type | Chimeric NKG2D | Vector Only | Tumor cell control |
| P815 | 30.32 ± 1.31 | 15.11 ± 0.94 | 5.53 ± 1.31 |
| P815/MIC-A | 140.19 ± 5.91 | 9.19 ± 3.30 | 2.85 ± 1.50 |
| Jurkat | 182.66 ± 18.31 | 7.64 ± 1.04 | 2.83 ± 1.33 |
| RPMI8866 | 2239.95 ± 19.59 | 280.41 ± 13.84 | 2.47 ± 2.47 |
| K652 | 2305.46 ± 75.84 | 1.91 ± 0.57 | 1.82 ± 1.39 |
| ECC-1 | 469.97 ± 18.79 | 2.67 ± 2.67 | 0.00 ± 0.00 |
| T Cells only | 13.67 ± 2.55 | 0.94 ± 0.54 | N. D. |

Amounts represent the average of three experiments

Chimeric NK cell receptor-bearing T cells are used to provide a means to attack tumor cells by activating host immunity and destroying tumor cells. In addition to tumors expressing NK cell receptor ligand, it is expected that analysis of ligand-deficient tumor cells will also result in tumor cell killing. For example, it has been demonstrated that ectopic expression of NK cell receptor ligands in tumor cell lines results in potent tumor rejection by syngeneic mice (Diefenbach, et al. (2001) Nature 413:165-171). However, using these same mice, subsequent challenge with tumor cell lines not expressing the ligands also resulted in tumor rejection. Using the mouse model as described herein, it is expected that NKG2D ligand-negative tumor cell lines, e.g., EL4, a B6 thymoma; RMA, a B6 T lymphoma derived from Rauscher virus-induced RBL-5 cell line (Karre, et al. (1986) Nature 319:675-678); and B16-BL6, a B6 melanoma derived from the B16-FO cell line (Hart (1979) Am. J. Pathol. 97:587-600), can be eliminated using the chimeric NK cell receptor-bearing T cells of this invention.

Although specific immunity may be obtained against tumors, local immunosuppressive mechanisms, such as regulatory T cells, prevents the function of tumor-specific T cells. The ability to remove these cells and enhance local anti-tumor immune function would be of great benefit for the treatment of cancer. In addition to activating host antitumor immunity, it has also now been found that adoptive transfer of chimeric NK cell receptor-bearing T cells can eliminate host regulatory T cells. Indeed, it was observed that treatment of mice with advanced tumors with chimeric receptor-bearing T cells results in a rapid loss of FoxP3+T regulatory cells from within the tumor microenvironment (within 3 days) and a destruction of advanced tumor cells. Accordingly, the chimeric NK cell receptors of the invention can also be used to enhance immunotherapy and vaccination approaches via elimination of host regulatory T cells.

Having demonstrated the activation of host anti-tumor immunity and tumor elimination using chimeric NK cell receptors expressed in the T cells of an animal model of cancer and likewise demonstrated human tumor cell killing with human chimeric NK cell receptors, the present invention embraces a nucleic acid construct for expressing a chimeric receptor in host T cells to reduce or eliminate a tumor. The nucleic acid construct contains a first nucleic acid sequence encoding a promoter operably linked to a second nucleic acid sequence encoding a chimeric receptor protein containing a C-type lectin-like natural killer cell receptor, or a protein associated therewith, fused to an immune signaling receptor having an immunoreceptor tyrosine-based activation motif of SEQ ID NO:1. In general, the C-type lectin-like NK cell type II receptor (or a protein associated therewith) is located at the C-terminus of the chimeric receptor protein of the present invention whereas the immune signaling receptor is at the N-terminus, thereby facilitating intracellular signal transduction from the C-type lectin-like NK cell type II receptor.

A C-type lectin-like NK cell receptor protein particularly suitable for use in the chimeric receptor of the present invention includes a receptor expressed on the surface of natural killer cells. The receptor can work alone or in concert with other molecules. Ligands for these receptors may or may not be expressed on the surface of one or more tumor cell types, e.g., tumors associated with cancers of the colon, lung, breast, kidney, ovary, cervix, and prostate; melanomas; myelomas; leukemias; and lymphomas (Wu, et al. (2004) *J. Clin. Invest.* 114:60-568; Groh, et al. (1999) *Proc. Natl. Acad. Sci. USA* 96:6879-6884; Pende, et al. (2001) *Eur. J. Immunol.* 31:1076-1086) and are not widely expressed on the surface of cells of normal tissues. Examples of such ligands include, but are not limited to, MIC-A, MIC-B, heat shock proteins, ULBP binding proteins (e.g., ULPBs 1-4), and non-classical HLA molecules such as HLA-E and HLA-G, whereas classical MHC molecules such as HLA-A, HLA-B, or HLA-C and alleles thereof are not generally considered strong ligands of the C-type lectin-like NK cell receptor protein of the present invention. C-type lectin-like NK cell receptors which bind these ligands generally have a type II protein structure, wherein the N-terminal end of the protein is intracellular. Exemplary NK cell receptors of this type include, but are not limited to, Dectin-1 (GENBANK accession number AJ312373 or AJ312372), Mast cell function-associated antigen (GENBANK accession number AF097358), HNKR-P1A (GENBANK accession number U11276), LLT1 (GENBANK accession number AF133299), CD69 (GENBANK accession number NM_001781), CD69 homolog, CD72 (GENBANK accession number NM 001782), CD94 (GENBANK accession number NM 002262 or NM_007334), KLRF1 (GENBANK accession number NM 016523), Oxidised LDL receptor (GENBANK accession number NM_002543), CLEC-1, CLEC-2 (GENBANK accession number NM 016509), NKG2D (GENBANK accession number BC039836), NKG2C (GENBANK accession number AJ001684), NKG2A (GENBANK accession number AF461812), NKG2E (GENBANK accession number AF461157), WUGSC:H_DJ0701016.2, or Myeloid DAP12-associating lectin (MDL-1; GENBANK accession number AJ271684). In particular embodiments, the NK cell receptor is human NKG2D (SEQ ID NO:2) or human NKG2C (SEQ ID NO:3).

Similar type I receptors which would be useful in the chimeric receptor of the present invention include NKp46 (e.g., GENBANK accession number AJ001383), NKp30 (e.g., GENBANK accession number AB055881), or NKp44 (e.g., GENBANK accession number AJ225109).

As an alternative to the C-type lectin-like NK cell receptor protein, a protein associated with a C-type lectin-like NK cell receptor protein can be used in the chimeric receptor protein of the present invention. In general, proteins associated with C-type lectin-like NK cell receptor are defined as proteins that interact with the receptor and transduce signals therefrom. Suitable human proteins which function in this manner include, but are not limited to DAP10 (e.g., GENBANK accession number AF072845; SEQ ID NO:4) and DAP12 (e.g., GENBANK accession number AF019562; SEQ ID NO:5).

To the N-terminus of the C-type lectin-like NK cell receptor is fused an immune signaling receptor having an immunoreceptor tyrosine-based activation motif (ITAM), (Asp/Glu)-Xaa-Xaa-Tyr*-Xaa-Xaa-(Ile/Leu)-Xaa$_{6-8}$-Tyr*-Xaa-Xaa-(Ile/Leu) (SEQ ID NO:1) which is involved in the activation of cellular responses via immune receptors. Similarly, when employing a protein associated with a C-type lectin-like NK cell receptor, an immune signaling receptor can be fused to the C-terminus of said protein (FIG. 1). Suitable immune signaling receptors for use in the chimeric receptor of the present invention include, but are not limited to, the zeta chain of the T-cell receptor, the eta chain which differs from the zeta chain only in its most C-terminal exon as a result of alternative splicing of the zeta mRNA, the delta, gamma and epsilon chains of the T-cell receptor (CD3 chains) and the gamma subunit of the FcR1 receptor. In particular embodiments, the immune signaling receptor is CD3-zeta (CD3ζ) (e.g., GENBANK accession number human NM 198053; SEQ ID NO:6), or human Fc epsilon receptor-gamma chain (e.g., GENBANK accession number M33195; SEQ ID NO:7) or the cytoplasmic domain or a splicing variant thereof.

In particular embodiments, a chimeric receptor of the present invention is a fusion between NKG2D and CD3ζ or Dap10 and CD3ζ.

As used herein, a nucleic acid construct or nucleic acid sequence is intended to mean a DNA molecule which can be transformed or introduced into a T cell and be transcribed and translated to produce a product (e.g., a chimeric receptor or a suicide protein).

In the nucleic acid construct of the present invention, the promoter is operably linked to the nucleic acid sequence encoding the chimeric receptor of the present invention, i.e., they are positioned so as to promote transcription of the messenger RNA from the DNA encoding the chimeric receptor. The promoter can be of genomic origin or synthetically generated. A variety of promoters for use in T cells are well-known in the art (e.g., the CD4 promoter disclosed by Marodon, et al. (2003) *Blood* 101(9):3416-23). The promoter can be constitutive or inducible, where induction is associated with the specific cell type or a specific level of maturation. Alternatively, a number of well-known viral promoters are also suitable. Promoters of interest include the B-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression (Barthel and Goldfeld (2003) J. Immunol. 171 (7):3612-9). Also, it may be further advantageous to use endogenous or exogenous non-coding regions to stabilize the mRNA.

For expression of a chimeric receptor of the present invention, the naturally occurring or endogenous transcriptional initiation region of the nucleic acid sequence encoding N-terminal component of the chimeric receptor can be used to generate the chimeric receptor in the target host. Alternatively, an exogenous transcriptional initiation region can be used which allows for constitutive or inducible expression, wherein expression can be controlled depending upon the target host, the level of expression desired, the nature of the target host, and the like.

Likewise, the signal sequence directing the chimeric receptor to the surface membrane can be the endogenous signal sequence of N-terminal component of the chimeric receptor. Optionally, in some instances, it may be desirable to exchange this sequence for a different signal sequence. However, the signal sequence selected should be compatible with the secretory pathway of T cells so that the chimeric receptor is presented on the surface of the T cell.

Similarly, a termination region can be provided by the naturally occurring or endogenous transcriptional termination region of the nucleic acid sequence encoding the C-terminal component, of the chimeric receptor. Alternatively, the termination region can be derived from a different source. For the most part, the source of the termination region is generally not considered to be critical to the expression of a recombinant protein and a wide variety of termination regions can be employed without adversely affecting expression.

As will be appreciated by one of skill in the art, in some instances, a few amino acids at the ends of the C-type lectin-like natural killer cell receptor (or protein associated therewith) or immune signaling receptor can be deleted, usually not more than 10, more usually not more than 5 residues. Also, it may be desirable to introduce a small number of amino acids at the borders, usually not more than 10, more usually not more than 5 residues. The deletion or insertion of amino acids will usually be as a result of the needs of the construction, providing for convenient restriction sites, ease of manipulation, improvement in levels of expression, or the like. In addition, the substitute of one or more amino acids with a different amino acid can occur for similar reasons, usually not substituting more than about five amino acids in any one domain.

The chimeric construct, which encodes the chimeric receptor according to this invention can be prepared in conventional ways. Since, for the most part, natural sequences are employed, the natural genes are isolated and manipulated, as appropriate (e.g., when employing a Type IT receptor, the immune signaling receptor component may have to be inverted), so as to allow for the proper joining of the various components. Thus, the nucleic acid sequences encoding for the N-terminal and C-terminal proteins of the chimeric receptor can be isolated by employing the polymerase chain reaction (PCR), using appropriate primers which result in deletion of the undesired portions of the gene. Alternatively, restriction digests of cloned genes can be used to generate the chimeric construct. In either case, the sequences can be selected to provide for restriction sites which are blunt-ended, or have complementary overlaps.

The various manipulations for preparing the chimeric construct can be carried out in vitro and in particular embodiments the chimeric construct is introduced into vectors for cloning and expression in an appropriate host using standard transformation or transfection methods. Thus, after each manipulation, the resulting construct from joining of the DNA sequences is cloned, the vector isolated, and the sequence screened to insure that the sequence encodes the desired chimeric receptor. The sequence can be screened by restriction analysis, sequencing, or the like.

The chimeric constructs of the present invention find application in subjects having or suspected of having cancer by decreasing FoxP3+T regulatory cells present in the tumor microenvironment and reducing the size of a tumor thereby preventing the growth or regrowth of a tumor in these subjects. Accordingly, the present invention further embraces chimeric NK receptor-bearing T cells and methods for using the same to decrease FoxP3+T regulatory cells present in the tumor microenvironment and reduce growth or prevent tumor formation in a subject.

The methods of this invention involve introducing a chimeric construct of the present invention into an isolated T cell and introducing into a subject the transformed T cell. Suitable T cells which can be used include, cytotoxic lymphocytes (CTL), tumor-infiltrating-lymphocytes (TIL) or other cells which are capable of killing target cells when activated. As is well-known to one of skill in the art, various methods are readily available for isolating these cells from a subject. For example, using cell surface marker expression or using commercially available kits (e.g., ISOCELL™ from Pierce, Rockford, IL). The T cells used in accordance with the invention are, in order of preference, autologous, allogeneic or xenogeneic, and the choice can largely depend on the urgency of the need for treatment. However, in particular embodiments, the T cells are autologous or isolated from the subject being treated.

While the present invention relates to the elimination of tumors, the chimeric NK receptors of the present invention can also be used in the treatment of other diseases where these ligands may be present. For example, the immune response can be down-modulated during autoimmune disease or transplantation by expressing these type of chimeric NK receptors in T regulatory or T suppressor cells. Thus, these cells would mediate their regulatory/suppressive function only in the location where the body has upregulated one of the ligands for these receptors. This ligand upregulation may occur during stress or inflammatory responses.

It is contemplated that the chimeric construct can be introduced into T cells as naked DNA or in a suitable vector. Methods of stably transfecting T cells by electroporation using naked DNA are known in the art. See, e.g., U.S. Pat. No. 6,410,319. Naked DNA generally refers to the DNA encoding a chimeric receptor of the present invention contained in a plasmid expression vector in proper orientation for expression. Advantageously, the use of naked DNA reduces the time required to produce T cells expressing the chimeric receptor of the present invention.

Alternatively, a viral vector (e.g., a retroviral vector, adenoviral vector, adeno-associated viral vector, or lentiviral vector) can be used to introduce the chimeric construct into T cells. Suitable vectors for use in accordance with the method of the present invention are non-replicating in the T cells. A large number of vectors are known which are based on viruses, where the copy number of the virus maintained in the cell is low enough to maintain the viability of the cell. Illustrative vectors include the pFB-neo vectors (STRATA-GENE@) disclosed herein as well as vectors based on HIV, SV40, EBV, HSV or BPV.

Once it is established that the transfected or transduced T cell is capable of expressing the chimeric receptor as a surface membrane protein with the desired regulation and at a desired level, it can be determined whether the chimeric receptor is functional in the host cell to provide for the desired signal induction (e.g., production of Rantes, Mipl-alpha, GM-CSF upon stimulation with the appropriate ligand).

Subsequently, the transduced T cells are introduced or administered to the subject to reduce the regulatory T cell population and activate anti-tumor responses in said subject. To facilitate administration, the transduced T cells according to the invention can be made into a pharmaceutical composition or made implant-appropriate for administration in vivo, with appropriate carriers or diluents, which further can be pharmaceutically acceptable. The means of making such a composition or an implant have been described in the art (see, for instance, *Remington's Pharmaceutical Sciences*, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed which does not ineffectuate the cells expressing the chimeric receptor. Thus, desirably the transduced T cells can be made into a pharmaceutical composition containing a balanced salt solution, preferably Hanks' balanced salt solution, or normal saline.

A pharmaceutical composition of the present invention can be used alone or in combination with other well-established agents useful for treating cancer. Whether delivered alone or in combination with other agents, the pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

A composition of the present invention can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular subject.

Desirably an effective amount or sufficient number of the isolated transduced T cells is present in the composition and introduced into the subject such that long-term, specific, anti-tumor responses are established to reduce the size of a tumor or eliminate tumor growth or regrowth than would otherwise result in the absence of such treatment. Desirably, the amount of transduced T cells introduced into the subject causes a 10%, 20%, 30%, 40%, 50%, 60%, 70%, 80%, 90%, 95%, 98%, or 100% decrease in tumor size when compared to otherwise same conditions wherein the transduced T cells are not present.

In embodiments drawn to an elimination or decrease in the regulatory T cell population of a subject, it is desired that the transduced T cells introduced into the subject cause a 10%, 20%, 30%, 40%, 50%, 60%, 70%, 80%, 90%, 95%, 98%, or 100% decrease in the number of FoxP3+T regulatory cells in the subject being treated as compared to a subject not receiving such treatment. In particular embodiments, the transduced T cells are administered to a subject having or suspected of having cancer so that the population of regulatory T cells is decreased at or near a tumor. A decrease in regulatory T cell population can be determined by, e.g., FACS analysis of a cell sample, wherein cells are sorted based upon the presence of cell surface markers. For example, regulatory T cells can be sorted and counted based upon the presence of CD4, CD25, and Fox3P.

The amount of transduced T cells administered should take into account the route of administration and should be such that a sufficient number of the transduced T cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced T cells desirably should be sufficient to provide in the subject being treated at least from about $1\times10^6$ to about $1\times10^9$ transduced T cells, even more desirably, from about $1\times10^7$ to about $5\times10^8$ transduced T cells, although any suitable amount can be utilized either above, e.g., greater than $5\times10^8$ cells, or below, e.g., less than $1\times10^7$ cells. The dosing schedule can be based on well-established cell-based therapies (see, e.g., Topalian and Rosenberg (1987) *Acta Haematol.* 78 Suppl 1:75-6; U.S. Pat. No. 4,690,915) or an alternate continuous infusion strategy can be employed.

These values provide general guidance of the range of transduced T cells to be utilized by the practitioner upon optimizing the methods of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

In particular embodiments, the chimeric nucleic acid construct further contains a suicide gene such as thymidine kinase (TK) of the HSV virus (herpesvirus) type I (Bonini, et al. (1997) *Science* 276:1719-1724), a Fas-based "artificial suicide gene" (Thomis, et al. (2001) *Blood* 97:1249-1257), or *E. coli* cytosine deaminase gene which are activated by gancyclovir, AP1903, or 5-fluorocytosine, respectively. The suicide gene is advantageously included in the nucleic acid construct of the present invention to provide for the opportunity to ablate the transduced T cells in case of toxicity and to destroy the chimeric construct once a tumor has been reduced or eliminated. The use of suicide genes for eliminating transformed or transduced cells is well-known in the art. For example, Bonini, et al. ((1997) *Science* 276:1719-1724) teach that donor lymphocytes transduced with the HSV-TK suicide gene provide antitumor activity in patients for up to one year and elimination of the transduced cells is achieved using ganciclovir. Further, Gonzalez, et al. ((2004) *J. Gene Med.* 6:704-711) describe the targeting of neuroblastoma with cytotoxic T lymphocyte clones genetically modified to express a chimeric scFvFc: ζ immunoreceptor specific for an epitope on L1-CAM, wherein the construct further expresses the hygromycin thymidine kinase (HyTK) suicide gene to eliminate the transgenic clones.

It is contemplated that the suicide gene can be expressed from the same promoter as the chimeric receptor or from a different promoter. Generally, however, nucleic acid sequences encoding the suicide protein and chimeric receptor reside on the same construct or vector. Expression of the suicide gene from the same promoter as the chimeric receptor can be accomplished using any well-known internal ribosome entry site (IRES). Suitable IRES sequences which can be used in the nucleic acid construct of the present invention include, but are not limited to, IRES from EMCV, c-myc, FGF-2, poliovirus and HTLV-1. By way of illustration, a nucleic acid construct for expressing a chimeric receptor can have the following structure: promoter→chimeric receptor→IRES→suicidal gene. Alternatively, the suicide gene can be expressed from a different promoter than that of the chimeric receptor (e.g., promoter 1→chimeric receptor→promoter 2→suicidal gene).

The following non-limiting examples are presented to better illustrate the invention.

Example 1: Mice and Cell Lines

C57BL/6 mice were purchased from the National Cancer Institute, and all animal work was conducted in accordance with standard guidelines.

Cell lines Bosc23, PT67, GP+E86, EG7 (H-2$^b$), and YAC-1 were obtained from the American Type Culture Collection (ATCC, Rockville, MD). RMA cells (H-2b) originated from a Rauscher virus-induced C57BL/6 T-cell lymphoma (Ljunggren and Karre (1985) *J. Exp. Med.* 162: 1745-1759). RMAS-S is a sub-line of RMA which lacks MHC class-I surface expression (Karre, et al. (1986) *Nature* 319:675-678). All packaging cells were grown in Dulbecco's modified Eagle medium (DMEM) with a high glucose concentration (4.5 gram/liter) supplemented with 10% heat-inactivated fetal bovine serum (FBS; Hyclone, Logan, UT), 20 U/mL penicillin, 20 μg/mL streptomycin, 1 mM pyruvate, 10 mM HEPES, 0.1 mM non-essential amino acids, 50 μM 2-mercaptoethanol. RMA, EG7, RMA-S and YAC-1 cells were cultured in RPMI plus the same supplements described above.

Example 2: Retroviral Vector Construction

The full-length murine NKG2D cDNA was purchased from Open Biosystems (Huntsville, AL). Murine CD3ζ chain, Dap10 and Dap12 cDNAs were cloned by RT-PCR using RNAs from ConA- or IL-2 (1000 U/mL)-activated spleen cells as templates. Mouse NKG2D ligands Rae-1p and H60 were cloned from YAC-1 cells by RT-PCR. All PCR reactions were performed using high-fidelity enzyme Pfu or PFUULTRA™ (STRATAGENE@, La Jolla, CA). The oligonucleotides employed in these PCR reactions are listed in Table 9.

TABLE 9

| No. | Primer | Sequence | SEQ ID NO: |
|---|---|---|---|
| 1 | 5' wtNKG2D | GCGAATTCGCCACCATGGCATTGATTCGTGATCGA | 8 |
| 2 | 3' wtNKG2D | GGCGCTCGAGTTACACCGCCCTTTTCATGCAGAT | 9 |
| 3 | 5' chNKG2D | GGCGAATTCGCATTGATTCGTGATCGAAAGTCT | 10 |
| 4 | 5' wtDAP10 | GCAAGTCGACGCCACCATGGACCCCCCAGGCTACC | 11 |
| 5 | 3' wtDAP10 | GGCGAATTCTCAGCCTCTGCCAGGCATGTTGAT | 12 |
| 6 | 3' chDAP10 | GGCAGAATTCGCCTCTGCCAGGCATGTTGATGTA | 13 |
| 7 | 5' wtDAP12 | GTTAGAATTCGCCACCATGGGGGCTCTGGAGCCCT | 14 |
| 8 | 3' wtDAP12 | GCAACTCGAGTCATCTGTAATATTGCCTCTGTG | 15 |
| 9 | 5' ATG-CD3ζ | GGCGTCGACACCATGAGAGCAAAATTCAGCAGGAG | 16 |
| 10 | 3' ATG-CD3ζ | GCTTGAATTCGCGAGGGGCCAGGGTCTGCATAT | 17 |
| 11 | 5' CD3ζ-TAA | GCAGAATTCAGAGCAAAATTCAGCAGGAGTGC | 18 |
| 12 | 3' CD3ζ-TAA | GCTTTCTCGAGTTAGCGAGGGGCCAGGGTCTGCAT | 19 |
| 13 | 5' Rae-1 | GCATGTCGACGCCACCATGGCCAAGGCAGCAGTGA | 20 |

TABLE 9-continued

| No. | Primer | Sequence | SEQ ID NO: |
|---|---|---|---|
| 14 | 3' Rae-1 | GCGG<u>CTCGAG</u>TCACATCGCAAATGCAAATGC | 21 |
| 15 | 5' H60 | GTT<u>AGAATT</u>CGCCACCATGGCAAAGGGAGCCACC | 22 |
| 16 | 3' H60 | GCG<u>CTCGAG</u>TCATTTTTCTTCAGCATACACCAAG | 23 |

Restriction sites inserted for cloning purposes are underlined.

Chimeric NKG2D was created by fusing the murine CD3 chain cytoplasmic region coding sequence (CD3'-CYP) to the full-length gene of murine NKG2D. Briefly, the SalI-EcoRI fragment of CD3'-CYP (with the initiation codon ATG at the 5' end, primer numbers 9 and 10) and the EcoRI-XhoI fragment of NKG2D (without ATG, primer numbers 2 and 3) were ligated into the SalI/XhoI-digested pFB-neo retroviral vector (STRATAGENE®, La Jolla, CA). Similarly, chimeric Dap10 was generated by fusing the SalI-EcoRI fragment of full-length Dap10 (primer numbers 4 and 6) to the EcoRI-XhoI fragment of CD3ζ-CYP (primer numbers 11 and 12). Wild-type NKG2D (primer numbers 2 and 3), Dap10 (primer numbers 4 and 5) and Dap12 (primer numbers 7 and 8) fragments were inserted between the EcoRI and XhoI sites in pFB-neo. In some cases, a modified vector pFB-IRES-GFP was used to allow co-expression of green fluorescent protein (GFP) with genes of interest. pFB-IRES-GFP was constructed by replacing the 3.9 kb AvrUScaI fragment of pFB-neo with the 3.6kb AvrII/ScaI fragment of a plasmid GFP-RV(Ouyang, et al. (1998) *Immunity* 9:745-755). Rae-1β (primer numbers 13 and 14) and H60 (primer numbers 15 and 16) cDNAs were cloned into pFB-neo. Constructs containing human NKD2D and human CD3ζ or murine Fc were prepared in the same manner using the appropriate cDNAs as templates.

Example 3: Retrovirus Production and Transduction

Eighteen hours before transfection, Bosc23 cells were plated in 25 cm² flasks at a density of 4×10⁶ cells per flask in 6 mL of DMEM-10. Transfection of retroviral constructs into Bosc23 cells was performed using LIPO-FECTAMINE™ 2000 (INVITROGEN™, Carlsbad, CA) according to the manufacturer's instruction. Viral supernatants were collected 48 and 72 hours post-transfection and filtered (0.45 μm) before use. For generation of large scale, high-titer ecotropic vectors, the ecotropic viruses produced above were used to transduce the dualtropic packaging cell PT67 in the presence of polybrene (8 μg/mL). After three rounds of transduction, PT67 cells were selected in G418 (1 mg/mL) for 7 days. Dualtropic vectors were then used to transduce ecotropic cell line GP+E86. Through this process, the virus titer from pooled GP+E86 cells generally was over 1×10⁶ CFU/mL. Concentration of retroviruses by polyethylene glycol (PEG) was performed according to standard methods (Zhang, et al. (2004) *Cancer Gene Ther.* 11:487-496; Zhang, et al. (2003) *J. Hametother. Stem Cell Res.* 12:123-130). Viral stocks with high titer (1~2×10⁷ CFU/mL) were used for transduction of T cells. Primary T cells from spleens of C57BL/6 (B6) mice were infected 18-24 hours after concanavalin A (ConA, 1 μg/mL) stimulation based on a well-established protocol (Sentman, et al. (1994) *J. Immunol.* 153:5482-5490). Two days after infection, transduced primary T cells (0.5~1×10⁶/mL) were selected in RPMI-10 media containing G418 (0.5 mg/mL) plus 25 U/mL rHuIL-2 for an additional 3 days. Viable cells were isolated using HISTOPAQUE®-1083 (Sigma, St. Louise, MO) and expanded for 2 days without G418 before functional analyses. NKG2D ligand-expressing RMA (RMA/Rae-1 and RMA/H60) or RMA-S(RMA-S/Rae-1β) cells were established by retroviral transduction with dualtropic vectors from PT67.

Example 4: Cytokine Production by Gene-Modified T Cells

Gene-modified primary T cells (10⁵) were co-cultured with an equal number of RMA, RMA/Rae-1β, RMA/H60 or YAC-1 cells in 96-well plates in complete media. After twenty-four hours, cell-free supernatants were collected. IFN-γ was assayed by ELISA using a DUOSET® ELISA kits (R&D, Minneapolis, MN). In some cases, T cells were cultured with equal numbers of irradiated (100 Gys) tumor cells for 3 days. Detection of other cytokines in culture was performed using a BIO-PLEX® kit (BIO-RAD®, Hercules, CA) based on the manufacturer's protocol.

Example 5: Flow Cytometry

For FACS analysis of NKG2D ligand expression, tumor cells were stained with mouse NKG2D-Ig fusion protein (R&D systems) according to manufacturer's instruction. Cell-surface phenotyping of transduced primary T cells was determined by direct staining with APC-anti-CD3e (clone 145-2C11; Pharmingen, San Diego, CA), PE-anti-NKG2D (clone 16-10A1; eBioscience, San Diego, CA) and FITC-anti-CD4 (Clone RM4-5; Caltag, Burlingame, CA) monoclonal antibodies. Cell fluorescence was monitored using a FACSCALIBER™ cytometer. Sorting of NKG2D ligand-expressing cells was performed on a FACSTARM™ cell sorter (Becton Dickinson, San Jose, CA).

Example 6: Cytotoxicity Assay

Three or four days after G418 selection (0.5 mg/mL), retroviral vector-transduced primary T cells were cultured in complete RPMI media containing 25 U/mL human IL-2 for an additional 2-3 days. Viable lymphocytes were recovered by centrifugation over HISTOPAQUE®-1083 (Sigma, St. Louis, MO) and used as effector cells. Lysis of target cells (RMA, RMA/Rae-1R, RMA/H60, EG7, RMA-S, RMA-S/Rae-1p, and YAC-1) was determined by a 4-hour $^{51}$Cr release assay (Sentman, et al. (1994) *supra*). To block NKG2D receptors, anti-NKG2D (clone: CX5, 20 μg/mL)

was included in those assays. The percentage of specific lysis was calculated as follows:

% Specific lysis=[(Specific $^{51}$Cr release−spontaneous $^{51}$Cr release)/(Maximal $^{51}$Cr release−spontaneous $^{51}$Cr release)]×100.

Example 7: Treatment of Mice with Genetically Modified T Cells

For the determination of direct effects of chimeric NKG2D-bearing T cells ($10^6$) on the growth of RMA or RMA/Rae-1β tumors, chimeric NKG2D- or vector-transduced T cells were mixed with tumor cells ($10^5$) and then injected s.c. into the shaved right flank of recipient mice. Tumors were then measured using a caliper, and tumor areas were calculated. Animals were regarded as tumor-free when no tumor was found four weeks after inoculation. For the rechallenge experiments, mice were inoculated with $10^4$ RMA cells on the shaved left flank. In other experiments, transduced T cells were injected intravenously the day before s.c. inoculation of tumor cells. Mice were monitored for tumor size every two days and were sacrificed when tumor burden became excessive.

Example 8: Statistical Analysis

Differences between groups were analyzed using the student's t-test. p values<0.05 were considered significant.

What is claimed is:

1. A nucleic acid construct which provides for the expression of a chimeric receptor which comprises:
a first nucleic acid sequence encoding a promoter operably linked to a second nucleic acid sequence encoding a chimeric receptor comprising a C-type lectin-like natural killer cell receptor, fused to a nucleic acid encoding an immune signaling receptor containing an immunoreceptor tyrosine-based activation motif of SEQ ID NO: 1,
wherein the C-type lectin-like NK cell type II receptor is Dectin-1, Mast cell function-associated antigen, HNKR-P1A, LLT1, CD69, CD69 homolog, CD72, CD94, KLRF1, CLEC-1, CLEC-2, NKG2D, NKG2C, NKG2A, or NKG2E.

2. The nucleic acid construct of claim 1, wherein the C-type lectin-like NK cell type II receptor is NKG2D, NKG2C, NKG2A, or NKG2E.

3. The nucleic acid construct of claim 1, wherein the C-type lectin-like NK cell type II receptor is NKG2D.

4. The nucleic acid construct of claim 1 wherein the C-type lectin-like NK cell type II receptor encoded by said nucleic acid construct comprises a human NKG2D polypeptide having the sequence set forth in SEQ ID NO:2 or is human NKG2C having the sequence set forth in SEQ ID NO:3.

5. The nucleic acid construct of claim 1, wherein the C-type lectin-like NK cell type II receptor comprises CD94.

6. The nucleic acid construct of claim 1, wherein the C-type lectin-like NK cell type II receptor comprises CD72.

7. The nucleic acid construct of claim 1, which further comprises a nucleic acid encoding DAP12 or DAP10.

8. The nucleic acid construct of claim 1, wherein the immune signaling receptor is CD3-zeta.

9. The nucleic acid construct of claim 1, wherein the immune signaling receptor encoded by said nucleic acid construct is CD3-zeta having the sequence set forth in SEQ ID NO:6, or is human Fc epsilon receptor-gamma chain having the sequence set forth in SEQ ID NO:7 or it comprises the cytoplasmic domain or a splicing variant thereof.

10. The nucleic acid construct of claim 1, further comprising a third nucleic acid sequence encoding a transmembrane domain.

11. The nucleic acid construct of claim 10, wherein the transmembrane domain comprises a CD8 transmembrane domain.

12. A cell comprising the nucleic acid construct of claim 1.

13. An isolated cell comprising the nucleic acid construct of claim 2.

14. An isolated cell comprising the nucleic acid construct of claim 3.

15. An isolated cell comprising the nucleic acid construct of claim 4.

16. An isolated cell comprising the nucleic acid construct of claim 5.

17. An isolated cell comprising the nucleic acid construct of claim 6.

18. An isolated cell comprising the nucleic acid construct of claim 7.

19. An isolated cell comprising the nucleic acid construct of claim 8.

20. An isolated cell comprising the nucleic acid construct of claim 9.

21. An isolated cell comprising the nucleic acid construct of claim 10.

22. An isolated cell comprising the nucleic acid construct of claim 11.

* * * * *

SEQUENCE LISTING

```
<160> NUMBER OF SEQ ID NOS: 23

<210> SEQ ID NO 1
<211> LENGTH: 19
<212> TYPE: PRT
<213> ORGANISM: Artificial Sequence
<220> FEATURE:
<223> OTHER INFORMATION: Consensus immunoreceptor tyrosine-based
      activation motif
<220> FEATURE:
<221> NAME/KEY: MISC_FEATURE
<222> LOCATION: (1)..(1)
<223> OTHER INFORMATION: Xaa denotes Asp or Glu
<220> FEATURE:
<221> NAME/KEY: MISC_FEATURE
<222> LOCATION: (2)..(3)
<223> OTHER INFORMATION: Xaa denotes any amino acid residue
<220> FEATURE:
<221> NAME/KEY: MISC_FEATURE
<222> LOCATION: (5)..(6)
<223> OTHER INFORMATION: Xaa denotes any amino acid residue
<220> FEATURE:
<221> NAME/KEY: MISC_FEATURE
<222> LOCATION: (7)..(7)
<223> OTHER INFORMATION: Xaa denotes Ile or Leu
<220> FEATURE:
<221> NAME/KEY: MISC_FEATURE
<222> LOCATION: (8)..(12)
<223> OTHER INFORMATION: Xaa denotes any amino acid residue
<220> FEATURE:
<221> NAME/KEY: MISC_FEATURE
<222> LOCATION: (13)..(15)
<223> OTHER INFORMATION: Xaa denotes 1 to 3 amino acid residues, wherein
      the amino acid can be any amino acid residue, where one or two
      positions can be absent
<220> FEATURE:
<221> NAME/KEY: MISC_FEATURE
<222> LOCATION: (17)..(18)
<223> OTHER INFORMATION: Xaa denotes any amino acid residue
<220> FEATURE:
<221> NAME/KEY: MISC_FEATURE
<222> LOCATION: (19)..(19)
<223> OTHER INFORMATION: Xaa denotes Ile or Leu

<400> SEQUENCE: 1

Xaa Xaa Xaa Tyr Xaa Xaa Xaa Xaa Xaa Xaa Xaa Xaa Xaa Xaa Xaa Tyr
1               5                   10                  15

Xaa Xaa Xaa

<210> SEQ ID NO 2
<211> LENGTH: 1575
<212> TYPE: DNA
<213> ORGANISM: Homo sapiens

<400> SEQUENCE: 2
```

```
tgaggacata tctaaatttt ctagttttat agaaggcttt tatccacaag aatcaagatc    60
ttccctctct gagcaggaat cctttgtgca ttgaagactt tagattcctc tctgcggtag   120
acgtgcactt ataagtattt gatggggtgg attcgtggtc ggaggtctcg acacagctgg   180
gagatgagtg aatttcataa ttataacttg gatctgaaga agagtgattt ttcaacacga   240
tggcaaaagc aaagatgtcc agtagtcaaa agcaaatgta gagaaaatgc atctccattt   300
tttttctgct gcttcatcgc tgtagccatg ggaatccgtt tcattattat ggtagcaata   360
tggagtgctg tattcctaaa ctcattattc aaccaagaag ttcaaattcc cttgaccgaa   420
agttactgtg gcccatgtcc taaaaactgg atatgttaca aaataactg ctaccaattt    480 tttgatgaga gtaaaaactg gtatgagagc caggcttctt gtatgtctca aaatgccagc   540
cttctgaaag tatacagcaa agaggaccag gatttactta aactggtgaa gtcatatcat   600
tggatgggac tagtacacat tccaacaaat ggatcttggc agtgggaaga tggctccatt   660
ctctcaccca acctactaac aataattgaa atgcagaagg gagactgtgc actctatgcc   720
tcgagcttta aaggctatat agaaaactgt tcaactccaa atacatacat ctgcatgcaa   780
aggactgtgt aaagatgatc aaccatctca ataaaagcca ggaacagaga agagattaca   840
ccagcggtaa cactgccaac cgagactaaa ggaaacaaac aaaaacagga caaaatgacc   900
aaagactgtc agatttctta gactccacag gaccaaacca tagaacaatt tcactgcaaa   960
catgcatgat tctccaagac aaaagaagag agatcctaaa ggcaattcag atatccccaa  1020
ggctgcctct cccaccacaa gcccagagtg gatgggctgg gggaggggtg ctgttttaat  1080
ttctaaaggt aggaccaaca cccagggat cagtgaagga agagaaggcc agcagatcag   1140
tgagagtgca accccaccct ccacaggaaa ttgcctcatg ggcagggcca gcagagag    1200 acacagcatg ggcagtgcct tccctgcctg tgggggtcat gctgccactt ttaatgggtc  1260
ctccacccaa cggggtcagg gaggtggtgc tgccctagtg ggccatgatt atcttaaagg  1320
cattattctc cagccttaag atcttaggac gtttcctttg ctatgatttg tacttgcttg  1380
agtcccatga ctgtttctct tcctctcttt cttccttttg gaatagtaat atccatccta  1440
tgtttgtccc actattgtat tttggaagca cataacttgt ttggtttcac aggttcacag  1500
ttaagaagga attttgcctc tgaataaata gaatcttgag tctcatgcaa aaaaaaaaa   1560 aaaaaaaaaa aaaaa                                                   1575

<210> SEQ ID NO 3
<211> LENGTH: 6098
<212> TYPE: DNA
<213> ORGANISM: Homo sapiens

<400> SEQUENCE: 3
gcagttatca tagagcacag tccctcacat cacacagctg cagagatgag taaacaaaga    60
ggaaccttct cagaagtgag tctggcccag gaccccaaagc ggcagcaaag gaaacctaaa  120
ggcaataaaa gctccatttc aggaaccgaa caggaaatat ccaagtagaa ttaaatcttt   180
caaaatcctt ccctgaatca tcaagggatt gataaaatat atgactgcca aggtaaaaca   240
ttaaatatat cttcaatatt attgttctag gatgtgcagt tgaatgcaga agggtgagga   300
aagattaggg aatattttgc acttgtgaga atcggagttc ataattggga tctaaaattc   360
taatatgaaa tcagaagact aatttttattc gggcattgtt caactgtaat ctgcggtcca   420
ctcatggaac attatattta ctgaaaatga aatggtatat tctgagagaa agattactag    480
agtagatgta gatttagagg ccagagttta tcattatgtt tccctgtgca tgtgggttct   540
```

```
ctagtatgta attctctagt atgtaatcct aatcaactct ctatctcccc tctctcagtg    600
cctctatttc tctccctgca ggtttactgc cacctccaga gaagctcact gccgaggtcc    660
taggaatcat ttgcattgtc ctgatggcca ctgtgttaaa aacaatagtt cttattcctt    720
gtaagcatat tcttgaaaga ttagaaggga acgttttact ttaatgcttg gaagtgcctc    780
aaaatatttc atactgttga agaatagaac tcttatttta ctgtttcttt caaagatcta    840
ttacttcatt tattttttata gaaaaagtta attttattaa agattgtccc cattttaaat    900
aacacacaaa gtttcaaagt aagaaactaa actcattatg gtttatctaa atattacttt    960
ttataaaaat cattttaatt tttctgttac agtcctggaa cagaacaatt cttccccaaa   1020
tacaagaacc cagaaaagta cattttattt ttcaaagttc tgatattagt acaatttgga   1080
accaaaagta atatggttat tctgaatttt tcacaacata ataacaaaa tcattgtaga   1140 gaacatgtgt ttatttttg tgtgtaatct atatatatgt atatacatac acacacaaag   1200
atattttctg atttcataat tcaaaggcat gctatagaag aaaagtattt agaaaaacaa   1260
attaattttt gaaagtggtt acatcaaata ctacaagaga tggtgaagtt tgtgctaaag   1320
tcttaaaaaa tgtttatttc aaaggtctat tactttatat attttttatag aaaaagttaa   1380 ttttattaaa gattctcccc attttaaata acacacaaag tttcaaagta agaaactaaa   1440
ctcgttatgg ttcatctaga tatcagttttt tataaaaatc attttaattt ttctattaca   1500
gtcctggagc agaacaattc ttccccgaat acaagaacgc agaaaggtac attttttattt   1560 tcaatgttct gatattagta caatttatat tttgtgtctg ttttaaggca tgtaaaagaa   1620
tagtggcatt tttgcagaaa ataagccata aattcagcca taaatatttg taagaaaga   1680 ttatgaggca gcatttcctt ttctccagtg agtagaaata ctcacttaaa atcattctac   1740
cctctttctc ccaattaaca gaggtttcct actgctgtga gatgatacca aataaataat   1800
tttactattc taaaaaagca gttgtgtatc agcgatgttc aacacatgtg tagagtgtat   1860
ttttgtttgt tcatttgctt tatatgggaa cacaattagg gaggagaggc taaccccttgt   1920 ctgtgcatgt gtgtatgact gactcagtta ttaaaaatat acattataa gcctgtaagg   1980 atgcgtaaat atgttaagca catatatgtt tatactgttg aaatatgtga actaattttc   2040 attttttaaaa attcatattg gtctaaatag taattcatat ctttattagc acgtcattgt   2100
ggccattgtc ctgaggagtg gattacatat tccaacagtt gttattacat tggtaaggaa   2160
agaagaactt gggaagagag tttgctggcc tgtacttcga agaactccag tctgctttct   2220
atagataatg aagaagaaat ggtaagatgt aaatgtttca aacattttat gaaaagcttc   2280
cttcagtgaa taatacatttt gtagaaaaca tccatatgtg tgtacatata tttatctcat   2340
atattttcaa gtgtatgtaa tattcaattg attgacttaa taatgttttt aaagttatat   2400
actgctaatg tacatttatt ttcagttttt gttttttcaag gaaaaccatg cttctataag   2460
tgctttgaat ccacaataaa ttttgctatc taatttttatc gggcatgata tcatctggtc   2520
atgcagattg atcacaaagt gaatgaatgc atgtgataca agtcagatca tgaaataaaa   2580
gtttccagct ctagcagttc caccccctgtg tatgccctca tcacttatcc tgactcctct   2640
ccaaaacgca gtcttgactt ttaatattat aaataatgat tgcctgttct tgaatttatt   2700
tatataaagg gaatcaaaca gtgtgaattt catgtctttt tcaatcctat ctgatatttg   2760
tgcaattcct ccatattatt gcagttatca gtagtatgtt actgttcact gctgtactat   2820
gtacaaagaa cagtaagaat ccattgagtc cttgtctctg gatggggaag tgggtctcat   2880
```

```
gccctcaggg acaaagagga ccctaggtgg tttacggtgc actgttagtc atgggtccc     2940
tttgctgatc ctcctcatcc acagccatcc tggtgtctct tggtatgaga aggaagcact    3000
ttctctagct ccatattggt agcaggtctc ctggtagatc atccttgcca gtggcaccag    3060
ccttgcctgg tattgtggag gggactctcc ttcgataccc tcctcctatt gccaggttgg    3120
gtgtagggaa acagcaggcc taggtcacct tcttctgtcg tgtggaggac ttaacatgct    3180
cacttggaca cttggttgat ccctgatgct agggtcccag acaatttcat ctttctcttt    3240
ccacctttca gagttctcca ttgcttttgt ctttcattaa cccagagtt tatagttgtt     3300
tttagtaggg agtagcagag agagacgagt ctacaccacc tggccaggac ccctgttatt    3360
ccgcaaaaac cgaatcggat aaaaattgag ggcttatcta gttaaagaat ggtgtggtac    3420
ccagaaaacc caatctgtag cttccatgtc atctatttct gaatgacaac ccctcaattc    3480
ccttctaaat ctccaactct gagaaatata gcacaaaaat agattgattt agtcacagta    3540
tctggagaaa tgaatgcaca gtatcaggaa acttattaaa accttcctg tgtttattct     3600
gttaattgga gtaactatta cattgcaaga attaaaatgt cttttattaac atgagaataa   3660
gaatgaaagt actaagtata aacgttgaag agttcattta aataaaaaat tcaaacattt    3720
atgaaagttt ttggcactgc aaatagtggt tttcaacttt aatatattgt ttttgtaatg    3780
ttttcataat tattatttaa gtgaaaatta tttcttttct tttagaaatt tctggccagc    3840
attttacctt cctcatggat tggtgtgttt cgtaacagca gtcatcatcc atgggtgaca    3900
ataaatggtt tggctttcaa acataagtaa gttcttttgt atggcgctat ataaaaaata   3960
tatataaagg ataaattcag aagaataata tgaataaatt tatgtggaat cattgacatg    4020
aagaaagatg tggaaagtta gtgaaatgtt gatataaata ttttacaata gaccatagta    4080
gtccatatat ttcaaccgct cattggtctg ctagtaacct tcttggttat cagatggacc    4140
aggggtgtcc catctttggc ttctgtgggc cacgttagaa gacgaatagt cttggcccac    4200
acatagaata cactaacact aacgatagct gacgagctaa aaaaaaaaaa aaatcacaga    4260
atgttttaag aaagtttacg tatttgtgtt gggccgcatt caaagctgtc ctgggtcacg    4320
tgcggcccat gggcagcgag ttggacaacc tcgagctgga ctatcaggga actgcagtgc    4380
ttgttttat taaaaagcca cgcttacttt tttacttaag aatatcctca aagcacaata    4440
atagtgctgt tggcatattg ctataatttt tttattacta gttattgttg tcaatctctt    4500
attgtgccta atttataaat taaactttat cacagttatg aatgtgtaga gaaaacataa    4560
tctctctata ggttctgcac tatctgccat tcaggcatc cactggggtc ttgaaacata     4620
tccctcgtgg atgaagaggg actactctgt tgagtgttca gaataatgac tcttactaat    4680
attatgaaaa atttaattac ccttttccat gaaattcttt tcttacagta catggaaaat    4740
gctttcgtct catgaatcat ttgcttaaaa tgtaacagaa tatggatttt tctccattac    4800
aggataaaag actcagataa tgctgaactt aactgtgcag tgctacaagt aaatcgactt    4860
aaatcagccc agtgtggatc ttcaatgata tatcattgta agcataagct ttagaagtaa    4920
agcatttgcg tttacagtgc atcagataca ttttatattt cttaaaatag aaatattatg    4980
attgcataaa tctgaaaatg aattatgtta tttgctctaa tacaaaaatt ctaaatcaat    5040
tattgaaata ggatgcacac aattactaaa gtacagacat cctagcattt gtgtcgggct    5100
cattttgctc aacatggtat ttgtggtttt cagcctttct aaaagttgca tgttatgtga    5160
gtcagcttat aggaagtacc aagaacagtc aaacccatgg agacagaaag tagaatagtg    5220
gttgccaatg tctcagggag gttgaaatag gagatgacca ctaattgata gaacgtttct    5280
```

```
ttgtgtcgtg atgaaaactt tctaaatttc agtaatggtg atggttgtaa ctttgcgaat      5340
atactaaaca tcattgattt ttaatcattt taagtgcatg aaatgtatgc tttgtacatg      5400
acacttcaat aaagctatcc agaaaaaaaa aagcctctga tgggattgtt tatgactgca      5460
tttatctcta aagtaatttt aaagattagc ttctttataa tattgacttt tctaatcagt      5520
ataaagtgtt tccttcaatg tactgtgtta tctttaattt ctctctcttg tattttgtat      5580
tttgggggat tgaagtcata cagaaatgta ggtattttac attatgctt  ttgtaaatgg      5640 catcctgatt ctaaaattcc ctttagtaat ttttgttgtt ataaatagaa atacaactga      5700
tgtctgcatt ttgattttat atctacttat tccactgatt ttatatattt aaatctatta      5760
tgtcaactat tgatttattt ctgggtgttc tatataacga gcaattttat ctgcaaatga      5820
tcacactttt attttttta  atccatgtgc tataacttag ttttattttc atttattttc      5880
actggctaag gttttatacc catagttgaa tagaaggcac aatcaaagtt ctttgtggat      5940
catatgcatc attttctggt tttggcaaaa aatacttcaa catgttatac atatttaaaa      6000
agcttggtgt ttttgcatc  ctatctttct catatcgaag cagttttata atcctatttt      6060
ctaatagatt ttatcaattg taacaatttt tattaatt                             6098

<210> SEQ ID NO 4
<211> LENGTH: 3000
<212> TYPE: DNA
<213> ORGANISM: Homo sapiens

<400> SEQUENCE: 4
aattcccagc cctggagctg gcattccagt gggaggccac tctcagtttc acttggtgac        60
ctttcacagc actgaccatg ttggccctat ttctcccctg cttgcttgct tttctatttt       120
attttattat tacatttta  ttgttagaga gagggtctca ttctgtcgcc caggctggag       180
tgcagtggca aagtggtgag atctcggctc actgcaacct ccacttgcct cagtctccca       240
agtagctggg attacaggag cctgacacca tgcccgggta atttttgtat ttttgtagag       300
acggggtttc accatattgg cttgaactcc tgatctcagg tgatccccc  accttggcct       360 cccaaagtgc tgggattaca ggcatgagcc actgcgtgg  cctctcccct gctttcaaga       420
tgccatgctc tcagggtcc  cctccctctt tctccatttc cctggcaaag ttcctcctct       480 tccccccattc agtgtgtgtt tgatagggg  cagaatcctg tctgcactca cttccttggt       540
gatctcaccc agtcttgtgg ctttaagtac catccataag ccatcaaccc ccaaatttac       600
atctccagac cagccttatc ccctgaactc ctaaatgcag tgaggttatt cagcatctcc       660
acagggagat tgtcaggcat ttccaaccct gtatgcccaa acctcgtcac tttccccgca       720
aacccacttc cctaccttc  atctctgcca gcagacactc ccatcttctc agcgtttcat       780
gccagaaggc ttggctgtct aggatccctc tcaaacacac ccacattcat ttaatcagca       840
aattttcttg gccctacctc caaaatattt ccagatctcc ctagcctgca cacccttgcc       900
acctgtcatt cccacttgga ccaggccagc agcctccctg gtctctctga ccctcccccct      960 gagttcgttc accaaaggca gtaacggaga caccccctca acacacacag gaagcagatg      1020
gccttgacac cagcagggtg acatccgcta ttgctacttc tctgctcccc cacagttcct      1080
ctggacttct ctggaccaca gtcctctgcc agaccctgc  cagaccccag tccaccatga      1140
tccatctggg tcacatcctc ttcctgcttt tgctcccagg tgaagccagt ggttacaggg      1200
gatggtaggc agagcgtttg tgagatgggt gcttgggtga cgtctgcagg gacgggtgat      1260
```

```
gaaagtgggg ttcttctccc tgcaccccctt cccttctggg agatccattc tgcttcaggg   1320
cctgggtcct tggggggcgga aggggtgag acagggagtt ctggagggc tgcctgttag    1380 cgtccccttc tcatggctgg gtctctgctg ccacttccaa tttcttgtca ctctccatgt   1440
ctctgggagt ccccttccca tgtggtcctg ttccatctct ccagcctgga gattacttct   1500
caggacacta ccttctcttc tctacaccct attttttggt ttgtttattt tgagatgggg   1560
tcttgctctg ttgtccaggc tggagtgcag tggcacaatc acggctcacg gcagccttga   1620
cttcctgggc tcaggtgatc ctcccagctc agcctcccga gtaactggga ttacaggtgt   1680
gaaccaacac ttccagctaa tttttgtatt tcttgtagag acgaggtctc actatgttgc   1740
ccaggctggt ctcgaactcc tgggctcaag cgatcttcct gcctcggcct cccaaagtgc   1800
tgggatgaca ggcgtgagcc acggtgccag gctgagcatt ctgttttgtg gaccttctct   1860
ccaccctcat ccaccttctt tctctttcca cagtggctgc agctcagacg actccaggag   1920
agagatcatc actccctgcc tttacccctg gcacttcagg tatcacttcc accccagaag   1980
cttggccaga ggctcccaga acaccccagt ggttctccag gtcaccatcc cacctcccgt   2040
cccaaaatca gaggatccgt gtccttctcc gagtcccaga atcagcgacc ccagcctgt   2100 gttcaggagc acccgtgtg cccgccgcac agccccgagg gtcctgggac accccagcct   2160
ctctgcatct gtctcccgtt tcatttccca agcgcaactc caaggaacct gggacccgcc   2220
ccctcgcagg ggacttcctc tctgcctgtg gccaaagcac agccccagga cgcagagctt   2280
gagttgtctc cctgttccgg cccccactct ccaggctctt gttccggatg tgggtccctc   2340
tctctgccgc tcctggcagg cctcgtggct gctgatgcgg tggcatcgct gctcatcgtg   2400
ggggcggtgt tcctgtgcgc acgcccacgc cgcagccccg cccaaggtga gggcggagat   2460
gggcggggcc tggaaggtgt atagtgtccc taggagggg gtcccaggga gggggccctt   2520
ggggaagccc tggaggaggt gctggggaaa ccctggggga ggtgcctggg gaaccctg    2580 aggaaaccc tgaagcaggg ggtccccagg gaagtggaga tatgggtggt caagcttcat    2640
gctttctctc ccctatcccc agaagatggc aaagtctaca tcaacatgcc aggcaggggc   2700
tgaccctcct gcagcttgga cctttgactt ctgaccctct catcctggat ggtgtgtggt   2760
ggcacaggaa cccccgcccc aacttttgga ttgtaataaa acaattgaaa cacctgtagt   2820
cgtattcttt ctcaaagaac cccagagttc ccaaagcctc cctcccatga actgtttctg   2880
gatccaaggc cccctcagaa ccccccacatg tccccatccc atcagcccaa ggatctggca   2940
taatgttttt tgtcttcatg tttattttag gagagtattg gggagcggtc tggtctctca   3000
```

<210> SEQ ID NO 5
<211> LENGTH: 604
<212> TYPE: DNA
<213> ORGANISM: Homo sapiens

<400> SEQUENCE: 5

```
ccacgcgtcc gcgctgcgcc acatcccacc ggcccttaca ctgtggtgtc cagcagcatc     60
cggcttcatg gggggacttg aaccctgcag caggctcctg ctcctgcctc tcctgctggc    120
tgtaagtggt ctccgtcctg tccaggccca ggccagagc gattgcagtt gctctacggt    180
gagcccgggc gtgctggcag ggatcgtgat gggagacctg gtgctgacag tgctcattgc    240
cctggccgtg tacttcctgg gccggctggt ccctcggggg cgaggggctg cggaggcagc    300
gacccggaaa cagcgtatca ctgagaccga gtcgccttat caggagctcc agggtcagag    360
gtcggatgtc tacagcgacc tcaacacaca gaggccgtat tacaaatgag cccgaatcat    420
```

```
gacagtcagc aacatgatac ctggatccag ccattcctga agcccaccct gcacctcatt    480
ccaactccta ccgcgataca gacccacaga gtgccatccc tgagagacca gaccgctccc    540
caatactctc ctaaaataaa catgaagcac aaaaaaaaaa aaaaaaaaaa aaaaaaaaaa    600
aaaa                                                                604

<210> SEQ ID NO 6
<211> LENGTH: 1677
<212> TYPE: DNA
<213> ORGANISM: Homo sapiens

<400> SEQUENCE: 6
gtcctccact tcctggggag gtagctgcag aataaaacca gcagagactc cttttctcct     60
aaccgtcccg gccaccgctg cctcagcctc tgcctcccag cctctttctg agggaaagga    120
caagatgaag tggaaggcgc ttttcaccgc ggccatcctg caggcacagt tgccgattac    180
agaggcacag agctttggcc tgctggatcc caaactctgc tacctgctgg atggaatcct    240
cttcatctat ggtgtcattc tcactgcctt gttcctgaga gtgaagttca gcaggagcgc    300
agacgccccc gcgtaccagc agggccagaa ccagctctat aacgagctca atctaggacg    360
aagagaggag tacgatgttt tggacaagag acgtggccgg gaccctgaga tgggggggaaa    420 gccgcagaga aggaagaacc ctcaggaagg cctgtacaat gaactgcaga agataagat    480 ggcggaggcc tacagtgaga ttgggatgaa aggcgagcgc cggaggggca aggggcacga    540
tggcctttac cagggtctca gtacagccac caaggacacc tacgacgccc ttcacatgca    600
ggccctgccc cctcgctaac agccagggga tttcaccact caaaggccag acctgcagac    660
gcccagatta tgagacacag gatgaagcat ttacaacccg gttcactctt ctcagccact    720
gaagtattcc cctttatgta caggatgctt tggttatatt tagctccaaa ccttcacaca    780
cagactgttg tccctgcact cttttaaggga gtgtactccc agggcttacg gccctggcct    840
tgggccctct ggtttgccgg tggtgcaggt agacctgtct cctggcggtt cctcgttctc    900
cctgggaggc gggcgcactg cctctcacag ctgagttgtt gagtctgttt tgtaaagtcc    960
ccagagaaag cgcagatgct agcacatgcc ctaatgtctg tatcactctg tgtctgagtg   1020
gcttcactcc tgctgtaaat ttggcttctg ttgtcacctt cacctccttt caaggtaact   1080
gtactgggcc atgttgtgcc tccctggtga gagggccggg cagaggggca gatggaaagg   1140
agcctaggcc aggtgcaacc agggagctgc aggggcatgg gaaggtgggc gggcagggga   1200
gggtcagcca gggcctgcga gggcagcggg agcctccctg cctcaggcct ctgtgccgca   1260
ccattgaact gtaccatgtg ctacaggggc cagaagatga acagactgac cttgatgagc   1320
tgtgcacaaa gtggcataaa aaacatgtgg ttacacagtg tgaataaagt gctgcggagc   1380
aagaggaggc cgttgattca cttcacgctt tcagcgaatg acaaaatcat ctttgtgaag   1440
gcctcgcagg aagacccaac acatgggacc tataactgcc cagcggacag tggcaggaca   1500
ggaaaaaccc gtcaatgtac taggatactg ctgcgtcatt acagggcaca ggccatggat   1560
ggaaaacgct ctctgctctg cttttttttct actgttttaa tttatactgg catgctaaag   1620
ccttcctatt ttgcataata aatgcttcag tgaaaaaaaa aaaaaaaaa aaaaaaa      1677

<210> SEQ ID NO 7
<211> LENGTH: 591
<212> TYPE: DNA
<213> ORGANISM: Homo sapiens
```

<400> SEQUENCE: 7

```
cagaacggcc gatctccagc ccaagatgat tccagcagtg gtcttgctct tactccttt      60 ggttgaacaa gcagcggccc tgggagagcc tcagctctgc tatatcctgg atgccatcct    120
gtttctgtat ggaattgtcc tcaccctcct ctactgtcga ctgaagatcc aagtgcgaaa    180
ggcagctata accagctatg agaaatcaga tggtgtttac acgggcctga gcaccaggaa    240
ccaggagact tacgagactc tgaagcatga gaaaccacca cagtagcttt agaatagatg    300
cggtcatatt cttctttggc ttctggttct tccagccctc atggttggca tcacatatgc    360
ctgcatgcca ttaacaccag ctggccctac ccctataatg atcctgtgtc ctaaattaat    420
atacaccagt ggttcctcct ccctgttaaa gactaatgct cagatgctgt ttacggatat    480
ttatattcta gtctcactct cttgtcccac ccttcttctc ttccccattc ccaactccag    540
ctaaaatatg ggaagggaga accccaata aaactgccat ggactggact c             591
```

<210> SEQ ID NO 8
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 8

```
gcgaattcgc caccatggca ttgattcgtg atcga                                35
```

<210> SEQ ID NO 9
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 9

```
ggcgctcgag ttacaccgcc cttttcatgc agat                                 34
```

<210> SEQ ID NO 10
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 10

```
ggcgaattcg cattgattcg tgatcgaaag tct                                  33
```

<210> SEQ ID NO 11
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 11

```
gcaagtcgac gccaccatgg acccccagg ctacc                                 35
```

<210> SEQ ID NO 12
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 12
ggcgaattct cagcctctgc caggcatgtt gat    33

<210> SEQ ID NO 13
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 13
ggcagaattc gcctctgcca ggcatgttga tgta    34

<210> SEQ ID NO 14
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 14
gttagaattc gccaccatgg gggctctgga gccct    35

<210> SEQ ID NO 15
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 15
gcaactcgag tcatctgtaa tattgcctct gtg    33

<210> SEQ ID NO 16
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 16
ggcgtcgaca ccatgagagc aaaattcagc aggag    35

<210> SEQ ID NO 17
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 17
gcttgaattc gcgaggggcc agggtctgca tat    33

<210> SEQ ID NO 18
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 18
gcagaattca gagcaaaatt cagcaggagt gc    32

<210> SEQ ID NO 19
<211> LENGTH: 35
<212> TYPE: DNA

```
<213> ORGANISM: Artificial Sequence
<220> FEATURE:
<223> OTHER INFORMATION: Synthetic oligonucleotide

<400> SEQUENCE: 19
gctttctcga gttagcgagg ggccagggtc tgcat                             35

<210> SEQ ID NO 20
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 20
gcatgtcgac gccaccatgg ccaaggcagc agtga                             35

<210> SEQ ID NO 21
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 21
gcggctcgag tcacatcgca aatgcaaatg c                                 31

<210> SEQ ID NO 22
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 22
gttagaattc gccaccatgg caaagggagc cacc                              34

<210> SEQ ID NO 23
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 23
gcgctcgagt cattttttct tcagcataca ccaag                             35
```